United States Patent
Shoseyov et al.

(10) Patent No.: US 10,011,846 B2
(45) Date of Patent: Jul. 3, 2018

(54) TRANSGENIC PLANTS CONTAINING SOLUBLE CELL WALL POLYSACCHARIDES

(75) Inventors: Oded Shoseyov, Karmei Yosef (IL); Ziv Shani, Mazkeret Batia (IL); Miron Abramson, Karmei Yosef (IL)

(73) Assignees: Futuragene Israel Ltd., Rehovot (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 12/450,443

(22) PCT Filed: Mar. 26, 2008

(86) PCT No.: PCT/IL2008/000419
§ 371 (c)(1),
(2), (4) Date: Sep. 25, 2009

(87) PCT Pub. No.: WO2008/120194
PCT Pub. Date: Oct. 9, 2008

(65) Prior Publication Data
US 2010/0137568 A1    Jun. 3, 2010

Related U.S. Application Data

(60) Provisional application No. 60/907,344, filed on Mar. 29, 2007.

(51) Int. Cl.
| | | |
|---|---|---|
| A01H 5/00 | (2018.01) | |
| C12N 15/82 | (2006.01) | |
| C12N 9/04 | (2006.01) | |
| C12N 9/10 | (2006.01) | |
| C12N 9/14 | (2006.01) | |
| C12P 7/10 | (2006.01) | |

(52) U.S. Cl.
CPC ....... *C12N 15/8246* (2013.01); *C12N 9/0006* (2013.01); *C12N 9/1055* (2013.01); *C12N 9/14* (2013.01); *C12P 7/10* (2013.01); *C12Y 101/99018* (2013.01); *Y02E 50/16* (2013.01)

(58) Field of Classification Search
CPC .................................................... C12N 9/0006
See application file for complete search history.

(56) References Cited

U.S. PATENT DOCUMENTS

| | | | | |
|---|---|---|---|---|
| 6,033,891 | A * | 3/2000 | Golightly ............. | C12N 9/0006 435/190 |
| 6,184,440 | B1 * | 2/2001 | Shoseyov et al. ............. | 800/290 |
| 2002/0138878 | A1 * | 9/2002 | Sticklen et al. .............. | 800/288 |
| 2010/0212050 | A1 | 8/2010 | Shoseyov et al. | |

FOREIGN PATENT DOCUMENTS

| | | |
|---|---|---|
| BR | PI0616845-0 | 7/2011 |
| CA | 2533925 | 2/2005 |
| EP | 1482033 | 12/2004 |
| EP | 1640457 | 3/2006 |
| EP | 2405009 | 1/2012 |
| WO | WO 97/29186 | 8/1997 |
| WO | WO 99/49047 | 9/1999 |
| WO | WO 00/09729 | 2/2000 |
| WO | WO/2000/011192 | * 2/2000 |
| WO | WO 00/11192 | 3/2000 |
| WO | WO/2000/009729 | * 3/2000 |
| WO | WO 03/020938 | 3/2003 |
| WO | WO 2006/032538 | 3/2006 |
| WO | WO 2006/040685 | 4/2006 |
| WO | WO 2006/074435 | 7/2006 |
| WO | WO 2007/039317 | 4/2007 |
| WO | WO 2008/120193 | 10/2008 |
| WO | WO 2008/120194 | 10/2008 |
| WO | WO 2008120194 | 10/2008 |

OTHER PUBLICATIONS

Henriksson et al, Biotechnology 78 (2000) 93-113.*
De Vries et al, Microbiology and Molecular Biology Reviews, Dec. 2001 497-522.*
Schaewen et al (The EMBO Journal vol. 9 No. 10 pp. 3033-3044, 1990).*
Raices et al (FEBS Letters, 369, 1995 233-238).*
Fang et al (Process Biochemistry 34 (1999) 957-961).*
Dumonceaux (Enzyme and Microbial Technology 29 (2001) 478-489).*
Chen et al (Euphytica 118: 185-195, 2001).*
Chen et al (Functional Plant Biology, 2004, 31,235-245).*
Casler (Theor Appl Genet (2002) 104:127-131).*
Hamelinck et al (Biomass and Bioenergy 28 (2005) 384-410).*
Mansfield et al (Applied and Environmental Microbiology, Oct. 1997, p. 3804-3809).*
Bao et al (FEBS 302(1) 1992, pp. 77-80).*
Raices et al (FEBS Letters 369 (1995) 233-238).*
Brenda—1.1.99.18: cellobiose dehydrogenase (acceptor). Brenda-enzymes.org. Retrieved from http://www.brenda-enzymes.org/al-l_enzymes.php?ecno=1.1.99.18&table=Synonyms (2016).*
Communication Relating to the Results of the Partial International Search dated Aug. 20, 2008 From the International Searching Authority Re.: Application No. PCT/IL2008/000419.
International Preliminary Report on Patentability dated Oct. 8, 2009 From the International Bureau of WIPO Re.: Application No. PCT/IL2008/000418.
International Preliminary Report on Patentability dated Oct. 8, 2009 From the International Bureau of WIPO Re.: Application No. PCT/IL2008/000419.
International Search Report dated Nov. 20, 2008 From the International Searching Authority Re.: Application No. PCT/IL2008/000419.
International Search Report dated Aug. 27, 2008 From the International Searching Authority Re.: Application No. PCT/IL2008/000418.

(Continued)

*Primary Examiner* — Lee A Visone

(57) ABSTRACT

The present invention provides a bio-fuel, wood or other product, such as a paper, textile or yarn product. The product can contain material from a transgenic plant over-expressing a nucleic acid molecule encoding an enzyme that causes the plant cell wall to be more water soluble than the wild type.

19 Claims, 15 Drawing Sheets

(56) References Cited

OTHER PUBLICATIONS

Written Opinion dated Nov. 20, 2008 From the International Searching Authority Re.: Application No. PCT/IL2008/000419.
Written Opinion dated Aug. 27, 2008 From the International Searching Authority Re.: Application No. PCT/IL2008/000418.
Boudet et al. "Lignins and Lignocellulosics: A Better Control of Synthesis for New and Improved Uses", Trends in Plant Science, XP002491107, 8(12): 576-581, Dec. 2003.
Farrokhi et al. "Plant Cell Wall Biosynthesis: Genetic, Biochimical and Functional Genomics Approaches to the Identification of Key Genes", Plant Biotechnology Journal, XP002491105, 4(2): 145-167, Mar. 2006.
Gaffe et al. "Characterization and Functional Expression of a Ubiquitously Expressed Tomato Pectin Methylesterase", Plant Physiology, XP002489392, 114(4): 1547-1556, 1997. Abstract, Fig.7.
Hasunuma et al. "Expression of Fungal Pectin Methylesterase in Transgenic Tobacco Leads to Alteration in Cell Wall Metabolism and a Dwarf Phenotype", Journal of Biotechnology, XP002489391, 111(3): 241-251, Aug. 5, 2004. p. 246, col. 2—p. 247, § 1.
Himmel et al. "Biomass Recalcitrance: Engineering Plants and Enzymes for Biofuels Production", Science, XP002491108, 315(5813): 804-807, Feb. 9, 2007.
Pelloux et al. "New Insights Into Pectin Methylesterase Structure and Function", Trends in Plant Science, XP022110814, 12(6): 267-277, Jun. 8, 2007. Fig.3a.
Pilling et al. "Expression of a Petunia Inflata Pectin Methyl Esterase in Solanum Tuberosum L. Enhances Stem Elongation and Modifies Cation Distribution", Planta, XP002366604, 210(3): 391-399, Feb. 1, 2000. Abstract, Fig.2.
Ragauskas et al. "The Path Forward for Biofuels and Biomaterials", Science, XP002491106, 311(5760): 484-489, Jan. 27, 2006.
Schmohl et al. "Pectin Methylesterase Modulates Aluminium Sensitivity in *Zea mays* and *Solanum tuberosum*", Physiologia Plantarum, XP002489393, 109(4): 419-427, Aug. 2000. Abstract, Fig.6.
Wen et al. "Effect of Pectin Methylesterase Gene Expression on Pea Root Development", The Plant Cell, XP000827852, 11: 1129-1140, Jun. 1, 1999. Abstract, Figs.1, 6.
Communication Pursuant to Article 94(3) EPC dated Jan. 26, 2010 From the European Patent Office Re.: Application No. 08720044.0.
Examination Report dated Apr. 12, 2011 From the Intellectual Property Office of New Zealand Re. Application No. 580623.
Response dated Mar. 8, 2011 to Communication Pursuant to Article 94(3) EPC of Sep. 9, 2010 From the European Patent Office Re.: Application No. 08720044.0.
Examination Report dated Sep. 13, 2010 From the Intellectual Property Office of New Zealand Re. Application No. 580623.
Response dated Mar. 9, 2011 to Examination Report of Sep. 13, 2010 From the Intellectual Property Office of New Zealand Re. Application No. 580623.
Official Action dated Jun. 7, 2011 From the US Patent and Trademark Office Re. U.S. Appl. No. 12/593,620.
Yermiyahu et al. "Root Elongation in Saline Solution Related to Calcium Binding to Root Cell Plasma Membranes", Plant and Soil, 191: 67-76, 1997.
Examination Report dated Jun. 28, 2011 From the Intellectual Property Office of New Zealand Re. Application No. 593692.
Response dated Jun. 5, 2011 to Examination Report dated Apr. 12, 2011 From the Intellectual Property Office of New Zealand Re. Application No. 580623.
Response dated Jul. 15, 2010 to Communication Pursuant to Article 94(3) EPC dated Jan. 26, 2010 From the European Patent Office Re.: Application No. 08720044.0.
Communication Pursuant to Article 94(3) EPC dated Sep. 9, 2010 From the European Patent Office Re.: Application No. 08720044.0.
Response dated Jun. 22, 2011 to Examination Report dated Apr. 12, 2011 From the Intellectual Property Office of New Zealand Re. Application No. 580623.
Examination Report dated Nov. 24, 2011 From the Intellectual Property Office of New Zealand Re. Application No. 580623.
Response dated Nov. 29, 2011 to Examination Report dated Nov. 24, 2011 From the Intellectual Property Office of New Zealand Re. Application No. 580623.
Translation of Office Action dated Oct. 17, 2011 From the State Intellectual Property Office of the People's Republic of China Re. Application No. 200880017574.2.
Examination Report dated Jul. 4, 2011 From the Intellectual Property Office of New Zealand Re. Application No. 580623.
Response dated Sep. 21, 2011 to Examination Report dated Jul. 4, 2011 From the Intellectual Property Office of New Zealand Re. Application No. 580623.
Examination Report dated Sep. 2, 2011 From the Intellectual Property Office of New Zealand Re. Application No. 593692.
Response dated Aug. 23, 2011 to Examination Report dated Jun. 28, 2011 From the Intellectual Property Office of New Zealand Re. Application No. 593692.
Examination Report dated Mar. 22, 2012 From the Intellectual Property Office of New Zealand Re. Application No. 593692.
European Search Report and the European Search Opinion dated Jan. 31, 2012 From the European Patent Office Re. Application No. 11003665.4.
Examination Report dated Jan. 17, 2012 From the Intellectual Property Office of New Zealand Re. Application No. 580623.
Translation of Office Action dated Aug. 15, 2012 From the State Intellectual Property Office of the People's Republic of China Re. Application No. 200880017574.2.
Translation of Search Report dated Aug. 15, 2012 From the State Intellectual Property Office of the People's Republic of China Re. Application No. 200880017574.2.
Requisition by the Examiner dated May 20, 2014 From the Canadian Intellectual Property Office Re. Application No. 2,681,614.
Decision on Rejection dated Feb. 13, 2014 From the State Intellectual Property Office of the People's Republic of China Re. Application No. 200880017574.2 and Its Translation Into English.
Translation of Office Action dated Jan. 5, 2013 From the State Intellectual Property Office of the People's Republic of China Re. Application No. 200880017574.2.
Translation of Office Action dated Apr. 27, 2013 From the State Intellectual Property Office of the People's Republic of China Re. Application No. 200880017574.2.
Translation of Search Report dated Jan. 5, 2013 From the State Intellectual Property Office of the People's Republic of China Re. Application No. 200880017574.2.
Office Action dated Aug. 15, 2012 From the State intellectual Property Office of the People's Republic of China Re. Application No. 200880017574.2 and Its Summary in English.
Communication Pursuant to Article 94(3) EPC dated Sep. 30, 2014 From the European Patent Office Re. Application No. 11003665.4.
Requisition by the Examiner and Examination Search Report dated Apr. 13, 2015 From the Canadian Intellectual Property Office Re. Application No. 2,681,614.
Notice of Reexamination dated Apr. 26, 2016 From the State Intellectual Property Application No. 200880017574.2. Office of the People's Republic of China Re.
Translation of Notice of Reexamination dated Apr. 26, 2016 From the State Republic of China Re. Application No. Intellectual Property Office of the People's 200880017574.2.
Decision for Reexamination dated Sep. 21, 2016 From the State Intellectual China Re. Application No. Property Office of the People's Republic of 200880017574.2.
Reexamination Decision (Decision No. 114121) dated Sep. 21, 2016 From the Patent Reexamination Board of the State Intellectual Property Office of the People's Republic of China Re. Application No. 200880017574.2 and Its Translation Into English.
Office Action dated Sep. 18, 2013 From the State intellectual Property Office of the People's Republic of China Re. Application No. 200880017574.2 and Its Translation Into English.
Fang et al. "Study on the Role of Cellebiose Dehydrogenase in Cellulose Degradation", Microbiology, 27(1): 15-18, 2000. Abstract in English.

(56) References Cited

OTHER PUBLICATIONS

Gao "Study on the Action Mechanism of Cellebiose Dehydrogenase in Cellulose and Lignin Degradations", Doctoral Dissertation of Shandong University, China, 3 P., 1998. Abstract in English.
Examination Report dated Sep. 22, 2017 From the Servico Publico Federal, Ministerio da Industria, Comercio Exterior e Sevicos, Instituto Nacional da Propriedade Industrial do Brasil Re. Application No. PI0808598.6. (7 Pages).
Examination Report dated Nov. 27, 2017 From the Instituto Nacional de la Propiedad Industrial, Administracion Nacional de Patentes de Argentina, INPI Argentina Re. Application No. P080101238 and Its Summary in English. (9 Pages).
Examination Report dated Feb. 28, 2018 From the Servico Publico Federal, Ministerio da Industria, Comercio Exterior e Sevicos, Instituto Nacional da Propriedade Industrial do Brasil Re. Application No. PI0808598.6. (6 Pages).
Translation dated Apr. 9, 2018 of Search Report and Technical Examination Report dated Feb. 28, 2018 From the Servico Publico Federal, Ministerio da Industria, Comercio Exterior e Sevicos, Instituto Nacional da Propriedade Industrial do Brasil Re. Application No. PI0808598.6. (7 Pages).
Technical Examination Report dated May 26, 2017 From the Instituto Nacional de la Propiedad Industrial, Administracion Nacional de Patentes de Argentina, INPI Argentina Re. Application No. P080101238 and Its Summary in English. (10 Pages).

\* cited by examiner

| Gene Name | No. of explants per experiment | No. of regenerating explants | Transgenic Plants | Precentage transformation |
|---|---|---|---|---|
| Cel-1-Isc | 300 | 29 | 3 | 1 |
| Cel-1-Isc | 300 | 30 | 12 | 4 |
| 4CL-Isc | 150 | 24 | 9 | 6 |
| 4CL-Isc | 150 | 14 | 7 | 5 |

Fig. 2 mRNA for chitin synthase (SEQ ID NO:1)

```
TTGACTTATAAAGAGAACACATATTTGTTTCGTTAAATAAATTAACGCGAAAACGAAAAACACAATGC
TGCCCTCTCAAAATCAAGAGTAGCATACTGTATGCGGTTATCTTGGCCATTAACTTTGGGATTGCTTTCGC
TCGTCATTATATTTCATGGGTGCTATTGGTATGCATTTGCCGCCTATTCTTGTACTTCTTGGCGCTGCGTCTCT
GTGGTATATTGCGTGGGTGCTGCTTATGCATCGTGTATACTTAGGTTTCAAGGAAGAAGAACTTGATAGAACCGTG
CCAAAGAACCTATGATGTTCCTCGTCACAGCGTATCGCGAGACGAAGGTTGTTGTTATTGTGATGGTGAGAA
AGTCCGTTACGATGCAAAAATAGACCCGAGGTTAGCAAGACTGTTGTTTCGTCATCAAAGATGCATATGAG
GGAAACTGCACGAACTACGAAAGTATAACCAGTATGATGAAACTTTCGTCATCAAAGATGACGTCGTATATC
GATTGGCATATAATAAGCCAAAGGATGTTACAATTTCAAGAAAATACATAATGGTATTGACGTCGTATATC
TCATAAAAAGTGAGAACGCGGGAAAACGTGATAGCGTTTGTGCTTGCACCGAACTCTTGCATACGGAAATCT
GTTCGAACATAGTGAAAACAGACATGCTATGATTGATTAGACGCGAATTAGACCTCATAGGTCTCGTTTG
GTACCGAAAGTTACCGTATGGTATTGATTATCCCGGTGTGTTGACGCCGGTTGGGTTATATTGATATTGAGAT
TTCTTGAAGAAATGAATTATCCCCTATCAAAAGGCTTGGATTTGGTTCCAAGGAATTGGTTATATAATCGGCCAG
GGGAAAGGTAAATCTCCCTATCAAAAGGCTTGGATTTGGTTCCAAGGAATTGGTTATATAATCGGCCAG
CATGTGATGCGCGTATACCAGAGCAGGATAACCGAAAAGGTAAGTTGTTGTTCGGGCGCTTGTTACGGTA
TTTACGTCCCCTACCATGTGCCGAACCTGAGTTGTTGAAAGAATTTAATACGCCTCCTCCCCAAACGCCGG
TTTGTTTCTTAGTATTCTTAGACAGGCCACTTCGTTGGTCGTCCTCTGATAGTCGCCTTATACAGTGCCTGTGAT
AGGAACGTCCGTTTTTAGACAGGCCACTTCGTTGGTCGCTCTTGATAGTCGTGCGGTCGCTTATACAGTGCCTCCAG
CAGTTTTTATCTCACAGAGGCGTCGTTGGGTCGTCCTCCTGATAGTCGTGCGGTCGCTTATACAGTGCCTCCAG
TGGAAAGAATTTGTATATTTCGAACGTATATATTTGATTATATTCAAGTTATTGGTTTTCTGTTTTCACCC
CTTTATCCATGGTTAACGTCTATATTTGATTATATTCTAGTTCTGCATCCCTGGTGCCCCTTGCATGGGTTC
TTTCTATCCCAATGGTTCTGTCTATCGTATTATTCGAATAACCTTGCATCCCTGGTCCCCTTGCATGGGTTC
TCTTAGAAATCGTCGTATCGTATTATTCCAAAGTTTTGATTATGGCATTTTTATCCATGGGTTTAAAACGACTT
ATCATTCAAGCAACTAAAATTACACAACAATAACCAATACACTTCTGTCTGAAACGTATCGTTGTAAATATCAATCACACA
AAAAAAAAAAAAAAAAAAAAAAAAAAA
```

Fig. 5a chitin deacetylase gene (SEQ ID NO:2)

```
ATGCACTTCTCGACCCTTTTTGGCGCGGCTACTGCTGCTCGCTGGCAGCACGAACGCAAGGTACG
TCGCCGGGCGGCTCCTTGGGCCCTTGACACAGACACCCAGACTGACACAACTCACAGCCCTCGCCCGT
CGCCAGGTTCCCCGTGGGCCACACCCATCCTCCAGTGCACCCAGCCTGGTTCGGTTGCCCTGACCTACGACG
ACGGTCCCCTTCACCCTTCACCCCGCAGCTCCTCGACATCTTGAAGCAGAAGACCGGTTCAGGGCGACCTTTTT
CGTCAACGGCAACAACTGGGCCAACATCGAGGCCGGATCCAACCCCGACAACCATCCGGCCATGCCGCCC
GACGGCCACCCTCGTCGGCACGTCCTCTCACACGTACCCGCGCAACACCCTCAACGGCTCTCCTCCGGACCGCA
TCTCCCAGATGCCGGCACGTCGAGGAGGCACGTACCCGCGCATCGACCTTCGCGCCCAAGTACACATGCCGCGC
GCCTACCTGTCGTGCCAGGACGCGGGCCAGGCCTCGGCGCCTGGATACCCAGCACCATCATCGACACC
AACCTCGACACCAAGGACTACGAGACTACGAGAACAAGCCCGAGACCACCTCTCGCCGAGAAGTTCAACA
ACGAGCTGAGCGCCGACGTCGCGACCGCCAACAGTACATTGTCCTCTCGCACGAGTCCACGAGACAGACGGT
CGTCTCCCTCACGCCAGAAGCTGATTGACACGTCAAGAGCAAGGGCTACCCGGCCACCGTCACCGTCGGGGAG
TGCCTCGGCGACGCCCCGGAGAACCTGGTACAAGGCCGTAA
```

Fig. 5b

A98R Hyaluronan synthase (SEQ ID NO:3)

ATGGGTAAAAATATAATCATAATGGTTTCGTGGTACACCATCATAACTTCAAATCTAATCGCGGTTGGAG
GAGCCTCTCTAATCTTGGCTCCGGCAATTACTGGGTATGTTCTACATTGGAATATTGCTCTCTCGACAAT
CTGGGGAGTATCAGCTTATGGTATTTTCGTTTTTGGGTTTTTCCTTGCACAAGTTTTATTTTCAGAACTG
AACAGGAAACGTCTTCGCAAGTGGATTTCTCTCAGACCTAAGGGTTGGAATGATGTTCGTTTGGCTGTGA
TCATTGCTGGATATCGCGAGGATCCTTATATGTTCCAGAAGTGCCTCGAGTCTGTACGTGACTCTGATTA
TGGCAACGTTGCCCGTCTGATTTGTGTGATTGACGGTGATGAGGACGATGATATGAGGATGGCTGCCGTT
TACAAGGCGATCTACAATGATAATATCAAGAAGCCCGAGTTTGTTCTGTGTGAGTCAGACGACAAGGAAG
GTGAACGCATCGACTCTGATTTCTCTCGCGACATTTGTGTCCTCCAGCCTCATCGTGGAAAACGGGAGTG
TCTTTATACTGGGTTTCAACTTGCAAAGATGGACCCCAGTGTCAATGCTGTCGTTCTGATTGACAGCGAT
ACCGTTCTCGAGAAGGATGCTATTCTGGAAGTTGTATACCCACTTGCATGCGATCCCGAGATCCAAGCCG
TTGCAGGTGAGTGTAAGATTTGGAACACAGACACTCTTTTGAGTCTTCTCGTCGCTTGGCGGTACTATTC
TGCGTTTTGTGTGGAGAGGAGTGCCCAGTCTTTTTCAGGACTGTTCAGTGCGTTGGGGGCCACTGGGT
GCCTACAAGATTGATATCATTAAGGAGATTAAGGACCCCTGGATTTCCCAGCGCTTTCTTGGTCAGAAGT
GTACTTACGGTGACGACCGCCGGCTAACCAACGAGATCTTGATGCGTGGTAAAAAGGTTGTGTTCACTCC
ATTTGCTGTTGGTTGGTCTGACAGTCCGACCAATGTGTTTCGGTACATCGTTCAGCAGACCCGCTGGAGT
AAGTCGTGGTGCCGCGAAATTTGGTACACCCTCTTCGCCGCGTGGAAGCACGGTTTGTCTGGAATTTGGC
TGGCCTTTGAATGTTTGTATCAAATTACATACTTCTTCCTCGTGATTTACCTCTTTTCTCGCCTAGCCGT
TGAGGCCGACCCTCGCGCCCAGACAGCCACGGTGATTGTGAGCACCACGGTTGCATTGATTAAGTGTGGG
TATTTTTCATTCCGAGCCAAGGATATTCGGGCGTTTTACTTTGTGCTTTATACATTTGTTTACTTTTTCT
GTATGATTCCGGCCAGGATTACTGCAATGATGACGCTTTGGGACATTGGCTGGGGTACTCGCGGTGGAAA
CGAGAAGCCTTCCGTTGGCACCCGGGTCGCTCTGTGGGCAAAGCAATATCTCATTGCATATATGTGGTGG
GCCGCGGTTGTTGGCGCTGGAGTTTACAGCATCGTCCATAACTGGATGTTCGATTGGAATTCTCTTTCTT
ATCGTTTTGCTTTGGTTGGTATTTGTTCTTACATTGTTTTTATTGTTATTGTGCTGGTGGTTTATTTCAC
CGGCAAAATTACGACTTGGAATTTCACGAAGCTTCAGAAGGAGCTAATCGAGGATCGCGTTCTGTACGAT
GCAACTACCAATGCTCAGTCTGTGTGA

Fig. 6 glucan synthase catalytic subunit (grd) gene    (SEQ ID NO:4)

```
ATTGGGGCGAGCCCTGCGGGTTCACTCCTATACCGCAGGGCAGTTCTTCATTTCAAAAATGATGTTCAG
ATGCCGCCCCGGAACCCGACGGCCAGCCGCCAACTGCGAGGTTAGGGCGGATGTATTTCAGTGCTGAAGG
TGACGTTCAGTCGGTGCTCTATGTGAACCTGACGATTCCGATTGGGGGCGATCCTGTTTGCCCTTCTCGCT
GATCCCAGAAGATGGTGACAGTTGCCGCCGGATACCTTGCCGCCGGCCTTCAGCATCATCATGTTGCTATCGCTCTGGTGTCTATATCG
TATGGCGGCAACGGATACCTTGCCGCCGGATACCTTGCCGCCGGCGAACTCTCCCTCGAAACGCTCTGGTGCTACACCTATTT
CACCTTCAGCTGATCTCGGTGCTTTATGCCATGGGGTCCATCCTCATACTTCTTCGCCGAACCGACTGG
TCAGCCGTTGCCGATCAGGAGAGCATATCTTGCAGGCAACCCGATGCGCCATGCCGCGCTCGTCGATGTGTTTA
TCTGCACTTACAACGAGCCGCTGAACGTTCGACGACACAAGACGCGGGGAGGTAAGAACCTATTGCGAAGCGCAGGC
TCGACTGCGGTCGTCTTCGTCTCCGACAACAAGACGCGGGCAAGGCAGGAGAAATCCAACATGCGCTCTCCACA
GTGAACTACGTCACACGTCCCGACAACAAGACGCAAGGCAGGAGAAATCAACATGCGCTCTCCAGGCAAACTT
CCAATGCGCTGGAAGAGTTCCGACTGTCATCATGTCCGAAGGTGGCTTCGTCCAGACGCCTCAATTCTATTC
CCTGCGGCGTGACGGTCTCTTTTCGGACCCGGAAGGTGGCTTCGTCCAGACGCCTCAATTCTATTC
AACAGTGATCCAATTCAGCACAATCTCGGTATAGACAAGAGCTTCGTGTCTCCGGCACCAGCTTCGTCGTCGTACGCCG
ACGATTTCCAGCCGGCAAGGATGCCGTTGGTTGCGCTTTTCGCGGATGCGCTTACCGGAAGACATGCTCTGACATATCGC
CGCCCGGTAAATGGTATTGGTGGTTTCCCTACGGATGCCGCTTACCGGAAGACATGCTCTGACATATCGC
CTGATGAAAGGGGATATGTCACGCGCTCACCCCGGCGGCGAACCGGCGCGTTGAATGTCGGCGGAAGGTG
TACCCGAATACATCACCAGCGCTATTTACGCTGACGCAGCCGCTGAATCTCAGATCGGGGCTTTTTCTGGCTG
ACCTCTCGGCGTGGAAATTTTACGCTGACGCAGGCGTCGCACTATCCCGCATTGCATGGACAGGGGCGTCGGGCGTGGCGTGC
TCGAAGCCGCTTATCGTGTCTGATGTTCATGAAGCTCGGCTCGGCCTGTCATCTCTTTGCGCTTTCTGGACCCTATTTCCACCTG
AGTTCGATGAGCTCAAGAGGACGCTTCCTCTTCATGAAGCTGGCCTGCTGGCGAAGTCACCCCGTTCAAAGTCACCGAAAAGGAGGAGACC
GATATCCGGCAAGAGGACGCTTCCCTCGTAAACCGTTCGGGGCCCGTTCAAAGTCACCGAAAAGGAGGAGACC
GATCCCAGGTCCGTGCTGCCTCACCCCCGACGGGGATTTTTTCGTCGTGACCCTGCTCTTCGTCCGCCGTCTC
CATCGTCCTGGCTGTCTATGTCTGGATGCCCTCGACCTGTGCCTCCGCCGCGCTCATTCAGGCTCGATC
TGGTCCGCCGTCGCGATGGTTATCGCGATTCACCAGCTTCATTTGCGGGCAGTTGCGGGTTCCCGTCCGGCA
AGGAGGAAATGATCGAGTGGATTTTCGCGGGTCCCATCCGCCGTCCGCGTTCCCAACGAGACCGGTGCTAT
CACCGGGCCTCGACGGAAAACATCACACTGGCTCCCGCTCCCGGTCCCATCCGCCGTCCGCGTTCCCAACGAGACCGGTGCTAT
CACCGGGCCTCGACGGAAAACATCACACTGGCTCCCGCTCCCCGGTCCCATCCGCCGTCCGCGTAAAGGATGTTTC
GTACCGGAGGCGACGAGCGCCCGGTCGATCGCGCCGTCATTTGCGCCTGTTGTTTCGCAAGGCTCCTGAAAATGTCGATTC
ATCAAGCGACCTGATGAAATCCATGCGGATTCTTCTCGCACGGGCATTCGGGTGA
ACAGGGCGACCTGATGAAATCCATGCGGATTCTTCTCGCACGGGCATTCGGGTGA
```

Fig. 7 gene for levansucrase (SEQ ID NO:5)

CTGCAGGCGATCATGGTTATTTATAAGGATTGTTATGTCCTGAAACCACACAACAGAACCAGAGTGATT
TCAAAAATAAAAAGCTATTAATATACAGACCTTCAGCAAGAAGTATTCGAAATAACCTGTGAGGATAT
TTATGTCAGATTATTATAATTATAAACCAACGCTCGTGCCGATGCATTGAAAGTTCATGAGGATGA
CCCAACCAACTCAACCGGTTATTGACATTGCATTCCCGGTAATGAGTGAAGAAGTCTTTATTTGGGAT
ACCATGCCATTGCGAGACTTCGACGGAGAGATTATCTCGTAAATGGTTGGTGTATTATTTTTACGCTAA
CAGCAGATCCGCAACACTGATAATCCGCGTATTTGTTATTGGTACTCACGCACCGGTAAAGACTGGATTTTTTGGC
GGTCCGGGTAATGGCGAAGGTGTGCGAACGCGTCACTCCGGGTGCAACCATTGCCAAAGTGCGCGGTAA
ATCGGGGGCGATATTGACCTGTATTATACCTGTGTCACTTGGAAGGTTTTCAGCAGGTTACATCACTTTTCTCTGCTGAC
AATCGTCACTTCCGATCAAGACGGAAGAGCAGAACGCTTTCTGAAGAAACCCAAGCCCATTCATTGACA
GGGACTATTTACCAGACGGCAAATTATATATGCTGTTTGCCCCGGGTTATGAAGATGTGGGTGGCAGGCTGT
GGAATGATGGCAAATTATATGCTGTTTGCCCCGGGTTATGAAGATGTGGGTGGCAAATATCAGGCAGGCTGT
CCAGGCTGAGATGGGTTGGCCAAAGACCTGTCAGGCAGTGAGTGAGTGGCAAATCCTGCCTCCGCTGATCACCGCTG
GTTGGTCTGTGTGGCCAAAGACTCAGATCAGACGCCCCTCATTTTGTCTTCTTCCAGGATGGTAAATACTATCTGTTCACCAT
TGGCCGTAAACGATCAGATCAGACGCCCCCCATTTGTCTTCTTCCAGGATGGTAAATACTATCTGTTCACCAT
TAGCCATAAGTACACTTTTGCCGATAAGAATAGCGCCGATGATGAATGATGCTAGGCAACCCGTCTTCACAACCTTTCC
CTTACCGGCCCTTACACGCCTTATGCCCGGGCTGGTCACTCTTATTGACAGTGTTCCGTGGAAAGG
AGACATATTCACACTATGGCGGTACTGAAGCTCCGACCGTAAAAATTCGTTGAAAGGCGATCGCTCATTT
TAAGGACTATCGCATTGGCGGTACTGAAGCTCCGACCGTAAAAATTCGTTGAAAGGCGATCGCTCATTT
ATTGTTGATAGCTTCGATTATGGATATATATTCCGGCAATGAAAGACATTACTTTAAAATAAGTCTGTTGTC
GATATC

Fig. 8

DNA SEQUENCE OF CDH
(SEQ ID NO:6)

```
ATGCTAGGTCGATCGTTACTTGCGCTTCTGCCTTTGCCTTCTGCCGTTCTCGCAGAGTGCCTCACAGT
TTACCGACCCTACCACAGAGGATTCCAGTTCCACTGGTATCACCGACCCTCGTTCATGACGTGACCTACGGCTT
CGTTTTCCCCCCTCTGGCCACCTCCCGGAGCGCAATCCACTGAGTTCATCGAGAGGTTGTTGCCCCATC
GCATCAAAATGGATTGGTATTGCCCTCGGTGCCCATGAACAACGACCTGCTACTTGTGGCTTGGGCCA
ACGGCAACCAAATTGTTCCTCCACTCGCTGGCTACTGGCTATGTACAGCCGACTGCATATACGGAAC
TGCCACTTTGACAACACTCCCTGAGACAACAATCAACTCACGCACTGGAAGTGGGTCTTTCAGTGTCAG
GGCTGCACTGAGTGGAACAATGGCGGCGGAATGACGTCACTAGCCAGGCGTTCTGGCGTGGGCATTCT
CCAACGTCGCGTCGACGACCCTCCGACCCGCAGAGTACCTTCAGCACGTACCTCGAGCACCGACTTCGGCTTCTT
CGGAATTGACTACTCGACGACAGCGCCAACTACCAGAACTACCTTAATGGCGACCCACTGCCAACCCTACG
ACCGAGACCAAGCCACAGAGCAACCCACACAAGCAGCTCAGTCACGACGACCACTGTTTCTGCTACACCTT
ACGATTACATCATGCTCGGTGTCCTGAGCCGGGTGGCCCTAGCACCAAGCAGACCGGTTGGAACGTATGTCGCTCCATGG
GAAGGTTCCTTCCGAGGTCTAACGAAGTTCGATATTCCCGCTTGGTCGAGTCCTTGTTCACTGATTCCAACC
GCTACTAGCAGTGGTGCAAAGACATCACAGTCTTCGCTGGTTCGGCGGGTACTTCGGTCAACGG
CCTTCTGGTGGTGCAAAGACATCACAGTCTTCGCTGGTTCCGGCGGGTACTTCGGTCAACGG
AGCTCCTACTACTGGTACCGCTAAGACGCAAGCTTTCGTCTCGTCCCCCAGTACGGACCACCCTTCGACCTGGACAAC
CACGCCCCGTACACCGAGCAAGCTTTCGTCTCCCCAGTACGGACCACCCTTCGACCTGATGGCCAGC
GCTACCTTGAGCAATCATTCAAACGTCGTCGTTCTCAACTTCTCAAAGGCTACAACCAGGCCACCAT
```

Fig. 12

DNA SEQUENCE OF CDH
(SEQ ID NO:6)

```
CAACGACACAACCCCAACTACACAAGGACCACCGTCTTCGGCTACAGCGCATTCGATTTCCTTAACGGCAAGCGT
GCTGGTCCAGTCGCCACCTACCTCCAGACGGCATTGGCTGCCCAACTTCACTTTCAAGACCAATGTCA
TGGTCTCGAACGTTGTCCGCAACGGCTCGCAGATCCTGGTGTCCAGACGAACGACCCGACGCTCGGCCC
CAACGGTTTCATCCCCGTGACCCGAAGGGCGTGTCATCCTCTGTGGCATTTGGCACTTCGCGC
ATTCTTCCAAAGCGGTATTGGCCCCACGGATATGATTCAGACTGTTCAGAGCAACGTTCAGACCGCGCCG
CCGGCTCCCGGCCAGAACCAGTGGATCAACCTCCCAGTCGGCATGAACGCACAGGACAACCCCTCGAT
CAACCTGGTCTTCACCCACCCCAGATCGATGCCTATGAGAACTGGGCTCTGGAGCAACCCGCGC
CCGGCTGACGCTGCACAGTACCTCCGGAACCAGTCCGGTGTCTTCGCAGGTGCTTCTCCAAACTCAACT
TCTGGCGGCGCATACTCTGGTTCGGATGGCTTTACCCCGTTATGCCCCAGGGACGGTGCGCCCGGCCAGC
CTCCGTGAACTCCTCGCTCGCCCTGAACGGACCAGATCTTCACGATCACCGTGTACCTCTCTACGGGC
ATCCAGTCGCGGTGGGCCATCGGCATGCAGCCTCCCGGCTACGGTGCTCACACCGCCGTGGCTCG
TGAATCCGGTCGACAAGACCGTGCTCCTGCAGGCGCTGCACGAGGTCGTCGTCTCGAACATAGGGTCGATTCC
CGGCCTGACGATGATCACGCCCGACACTGGGTCTCCGACGTCAGGCAGATCGGCTCATCTCCCCAGAGCGCCGG
ACGATGAACTCGAACCACTCTTTGGCACGACAACCTGTTTATCGTCGCAGCAGTATCATTCCCCACCTGCCCAC
GAACGTCAAGGTCTTCAGGGCACGCTCATGTCTGCCCGCCGAGCAGGCGGCCGAAGATCCTCGCGCTTGCGGGA
GGTCCTTGA
```

Fig. 12 (cont.)

DNA SEQUENCE OF GFAT
(SEQ ID NO:7)

ATGTGTGGCATCTTTGGAGCAGTGTCAAACAATAACTCTATCGAGTGTCAATAAGGGTATTCAAAAGC
TAGAATATCGCGGGTATGATTCGTGCGGTATTGATTGTGCGGTATTGCGTATGCAGATGGAGACGGTGTAATCGAGCGTATACG
TTCAATTGATGGAATTGAAGATCTTCGAAGAAAACACTTGAAGAATCCTCACCGGTTGCCATTGCTCAC
TCTAGGTGGAGCACCACGGAATTCCATCGGTGGTGAACGACACATCCTCATATTTCTCGCGGAACCAGTG
GGTGTGAGTCTCGTATCGCGGTAGTCCACAATGGTATTCATTGAAAACTATCAGCAGATCCGAAAATATCT
CATCAATTCGGTTATACGTTTGATAGTCAAACGGACAGAGGTCATTGCACATTGATCGATTCTCAG
TACAATGGGAATATCTTGCACACCCGTCAAAATGGCTGTCAAGCACCTGAAGGCTCTTATGCAATTGCAG
TTATGTGTCATAAAGAGTCTGGTAAAATAGTCGTGGCGAAACAGAAGTCACCCCTCGTACTTGGAATCGG
CTCAGATGGTGCTTACTACATTGCTTCGGACGTGCTGGCGTATGACCATTACGATCCTCGATAACTTGTTTATATTTCA
GATGGTTTCTCCCAGAACTATCTCCAGGGAGTATGAACAAACTAGTATGTCTCGATAAATAAAGGGTTCATCATTACATGATTAA
ATGAAGTAGAGGAGGACGTTGAAATGGAACAATCAGTATTCTAAACATGGACAACATCGGAGAATCCGATACTGCTGTGTGACAAGTTATC
GGAAATTAATGAGCAACCAATCAGTGAAATCTTCAAAAATAAAAATAAAAATCCTGATACTGCTGTGTGACAAGTTATC
GGTGATTTGGCATGCTTGTAGGGAAAACAGTGGATAGAGAACATCCGAGAATCCCCGTGATCCACATCCGCAG
ACGCCGGTCTGTGTAGGGAAAACAGTGGATAGAGAACATCCGAGAATCCCCGTGATCCACATCCGCAG
CGAATACGAACCTACAATTCCGAGAGCGAACACATTGTAATCACTATTCACAGTCGTTGTGCATTGCAACTCGC
GACACGATAGCGGCTTTGTCCGCGGAGAGCGGTAATGAAGTACATAAGCGGGTGATTTGTTTGACAAATGACGAAATGAAAC
CAAAGAGCACTCTTGTCCGCGGAGAGCGGTTATGAAGTACTCGTACATGCTGGCAAACGTATTGGCAAATAAAACC
ATCAAGAGGCGTTTACCTCACAGCTCGTACTCACAGTCGTTATGAAGTACTCGTACATGCTGGCAAACGTATTGGCAAATAAAACC
GATGATTTGCTGGGAGACCTCCCACAGCAATAGAACGGGTGATTTGTTTGACAAATGACGAAATGAAAC
GATGGGCTGACGAAATTTGCACTGCGAAATCTGCGATCTTCCTGGAAGAGAGGGCTTCCTGGGAGGTGAGTTG
CTTTGAGGGAGCGCTGAAGCTCAAAGAAATCTCTTACATTCATGCAGCAGAGGACTAAACGCACCAGTGC
AAACATGGTCCCCTCGCACTCCTTGATGACAAGTGCTTGCGAGGAACGTTACGGTATACGCCATAGTAGACCA
TGGACCATATCAAAGCAAATATTGACGAAGTGCTTGCGAGGAACGTTACGGTATACGCCATAGTAGACCA
GTATGTGAACATTGAGCCCAGGAACGCCTTCACGTCGTCAAGTTCCGTTTGTATCCAAAGAATTTTCT
CCGATAATTCACACTATCCGATGCAACTGCGCTATTACGTGCAATTACGTGGCAATTAAGCTTGGAAGAACGTTG
ACAAACCAAGGAATCTTGCAAAATCCGTGACTACCTTTTAA

Fig. 13

AMINO ACID SEQUENCE OF GFAT
(SEQ ID NO:8)

MCGIFGAVSNNNSIEVSIKGIQKLEYRGYDSCGIAYADGDGVIERIRSIDGIEDLRKKTLEESSPVAIAH
SRWSTTGIPSVVNAHPHISRGTSGCESRIAVVHNGIIENYQQIRKYLINLGYTFDSQTDTEVIAHLIDSQ
YNGNILHTVQMAVKHLKGSYAIAVMCHKESGKIVVAKQKSPLVLGIGSDGAYIASDVLALPTNKVVYIS
DGFSAELSPGSMTIYDPDGNEVEYEVEDVEMEQTSMSLDNFDHYMIKEINEQPISILNTIKNKGFYAEIF
GDLAHEIFQKIDNILILACGTSYHAGLVGKQWIETIARIPVDVHIASEYEPTIPRANTLVITISQSGETA
DTIAALQRAQNAGMIYTLCICNSPKSTLVRESVMKYITKCGSEVSVASTKAFTSQLVVLYMLANVLANKT
DDLLGDLPQAIERVICLTNDEMKRWADEICTAKSAIFLGRGLNAPVAFEGALKLKEISYIHAEGELGGEL
KHGPLALLDDKIPVIVTVADHAYLDHIKANIDEVLARNVTVYAIVDQVNIEPQERLHVVKVPFVSKEFS
PIIHTIPMQLLSYYVAIKLGKNVDKPRNLAKSVTTF

TRANSGENIC PLANTS CONTAINING SOLUBLE CELL WALL POLYSACCHARIDES

RELATED APPLICATIONS

This application is a National Phase Application of PCT Patent Application No. PCT/IL2008/000419 having International Filing Date of Mar. 26, 2008, which claims priority from U.S. Provisional Patent Application No. 60/907,344, filed on Mar. 29, 2007. The contents of the above Applications are all incorporated herein by reference.

FIELD OF THE INVENTION

The present invention relates generally to plants genetically engineered to display altered structure, morphology or phenotype. The altered structure, morphology or phenotype is generally associated with the cell walls of the plants expressing soluble polysaccharides that will intercalate during cell wall synthesis or modified cell wall polymers to become more soluble. Plants with such characteristics enable a more rapid penetration of solvents and enzymes or more rapid disassembly of the cell wall, leading to products, such as bio-fuel or wood products. These products can be processed more rapidly and cheaply.

BACKGROUND OF THE INVENTION

In the biomass-to-ethanol processes the most energetic consuming step is the pretreatment. This process area converts, by hydrolysis reactions, most of the hemicellulose portion of the feedstock to soluble sugars, primarily xylose, mannose, arabinose, galactose and glucose. A small portion of the cellulose is converted to glucose. This conversion is accomplished using dilute sulfuric acid and high temperature (for example, 190° C.). These conditions also solubilize some of the lignin in the feedstock and expose the cellulose for subsequent enzymatic hydrolysis. From that point, cellulose undergoes saccharification and fermentation, converting cellulose to ethanol. Allowing the raw material plant to be susceptible to liquid penetration or cell wall disassembly will make this process cheaper and quicker.

Similarly, the process to make wood, paper, fiber or textile products involves the penetration of solvents and enzymes into the raw material. A more rapid penetration of these solvents and enzymes will also make these processes cheaper and quicker. The present invention satisfies this need, and provides additional advantages as well.

SUMMARY OF THE INVENTION

The present invention provides a bio-fuel, wood or other product, such as a paper, textile or yarn product. The product can contain material from a transgenic plant over-expressing a nucleic acid molecule encoding an enzyme that catalyzes the synthesis of a polysaccharide that is water soluble and/or will melt or dissolve upon acidic or alkaline treatment. Alternatively, the polysaccharide can be converted into a second polysaccharide that is water soluble and/or will melt or dissolve upon acidic or alkaline treatment.

More particularly, the present invention relates to transgenic plants expressing a cell wall modulation transgene or gene construct that results in a transgenic plant having altered structure or morphology. The cell wall modulation transgene can be a gene encoding an enzyme that catalyzes the synthesis of a water-soluble polymer, especially in the cell wall, especially where such a polymer intercalates into the normal cell wall. An example of such an enzyme is levansucrase. An example of such a polymer is fructan.

Alternatively, the transgene is a gene encoding an enzyme that catalyzes the synthesis of a polymer which is then converted to a water-soluble polymer. An example of such an enzyme is chitin synthase. An example of such a polymer is chitin which may be converted to chitosan. Another example of such an enzyme is a certain enzyme that can incorporate one or more units of N-acetylglucosamine into a cellulose polymer thus creating a chitin-cellulose polymer, which may be converted into a chitosan-cellulose polymer. In addition, the chitin-cellulose polymer, without conversion, is an example of the subject invention because it has a less high ordered or crystalline structure than the cellulose polymer and, therefore, is more water soluble.

Finally, the transgene of the subject invention can be an enzyme that can make an existing polymer in the plant, more specifically and preferably in the cell wall, more water soluble. An example of such an enzyme is cellobiose dehydrogenase (CDH), which can make cellulose polymers more water soluble than their natural forms.

In another aspect, the invention provides a transgenic plant over-expressing a nucleic acid molecule encoding an enzyme that catalyzes the synthesis of a polysaccharide that is in the cell wall and melts or dissolves upon acidic or alkaline treatment, provided that the enzyme is not hyaluronan synthase and the polysaccharide is not hyaluronan.

BRIEF DESCRIPTION OF THE DRAWINGS

FIG. 2 shows the frequency of transgenic events with two different constructs using the 4CL and cell promoters. There was a slightly higher percentage of transformation achieved using the 4CL promoter compared to the cell promoter.

FIG. 5A shows the chlorella virus CHS mRNA for chitin synthase (SEQ ID NO:1; complete cds; gi|18149184|dbj|AB071039.1|).

FIG. 5B shows the colletotrichum lindemuthianum chitin deacetylase gene (SEQ ID NO:2; partial cds; gi|49790329|gb|AY633657.1|)).

FIG. 6 shows the paramecium bursaria chlorella virus 1, A98R Hyaluronan synthase (SEQ ID NO:3; gi|52221425: 50903-52609).

FIG. 7 shows the Agrobacterium sp. ATCC 31749 beta 1,3 glucan synthase catalytic subunit (crd) gene (SEQ ID NO:4; complete cds; gi|40556679|gb|AF057142.2|)

FIG. 8 shows the *E. amylovora* lsc gene for levansucrase (SEQ ID NO:5; gi|433558|emb|X75079.1|).

FIG. 10 shows the saccharification comparison between wild type and two 4cl-has independent lines.

FIG. 12 shows the DNA sequence of cellobiose dehydrogenase (CDH; SEQ ID NO:6)).

FIG. 13 shows the DNA sequence (SEQ ID NO:7) and amino acid sequence (SEQ ID NO:8) of GFAT.

DETAILED DESCRIPTION OF THE INVENTION

Figure 1:
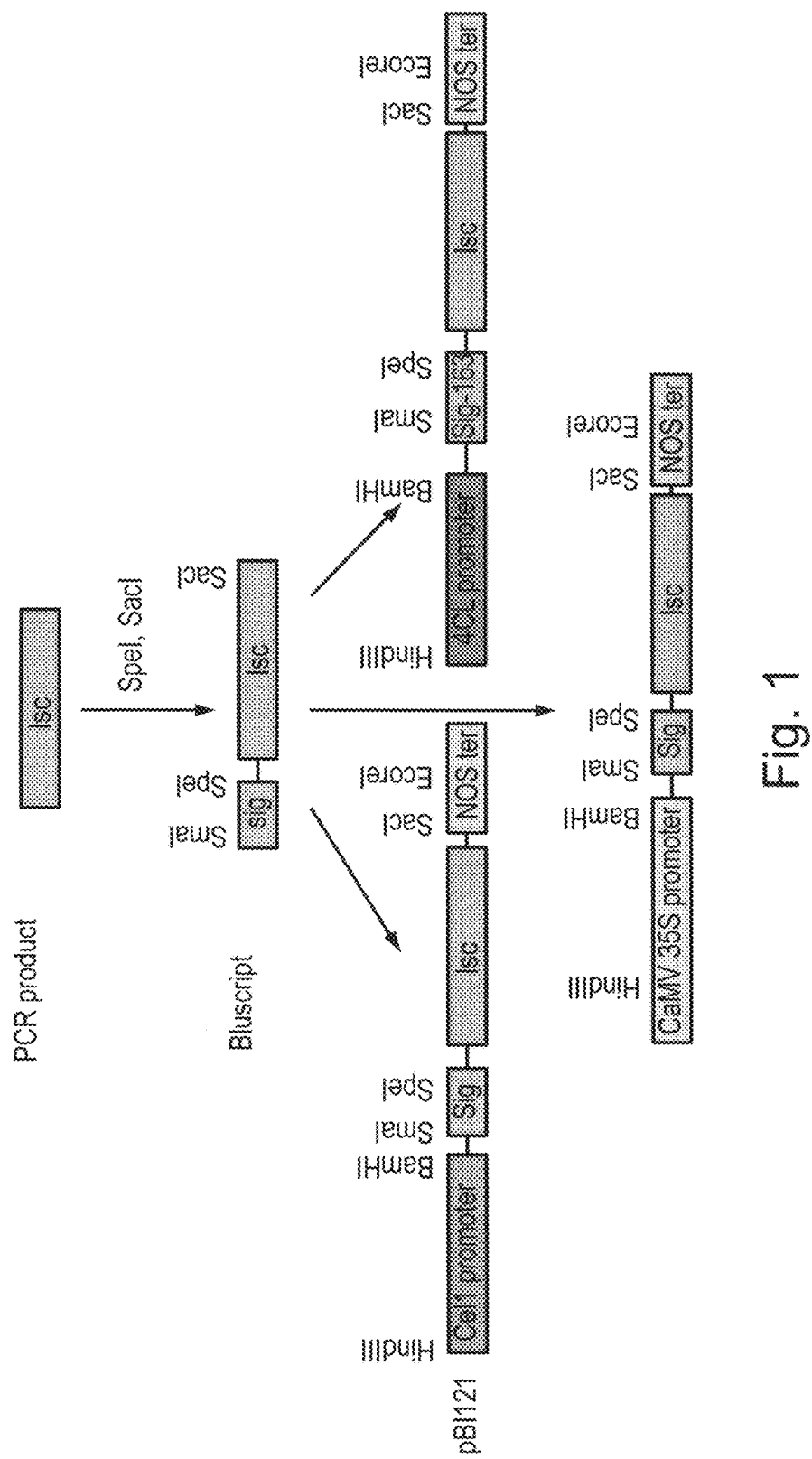
FIG. 1 shows three constructs containing three different promoters that express the Lsc gene at different stages of the plant cell wall development were prepared for *Eucalyptus* hybrid (*E. europhylla*×*E. grandis*) transformation.
Figure 3A:
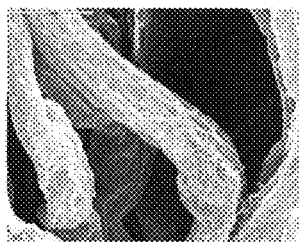
FIG. 3 shows scanning electron microscopy of tissues from the third internode shows significant difference in cell wall structure between wild type and the Lsc expressing transgenic plants: A-C different magnifications of 4CL-Lsc cells; D-F cell-Lsc cells; G-I wild type cells.
Figure 3B:
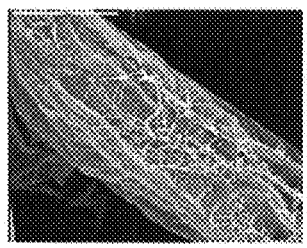
Figure 3C:
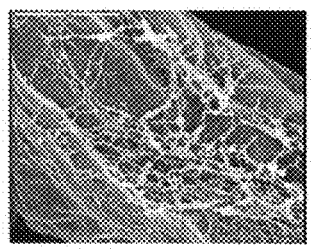
Figure 3D:
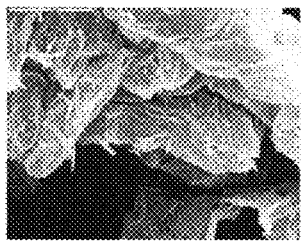
Figure 3E:
Figure 3F:
Figure 3G:
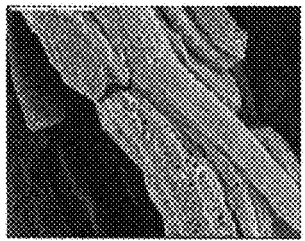
Figure 3H:
Figure 3I:
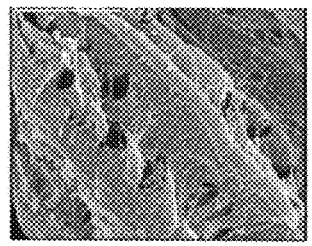

The present invention is directed to a product that contains material from a transgenic plant over-expressing a nucleic acid molecule encoding an enzyme that catalyzes the synthesis of a first polysaccharide that is water soluble and/or will melt or dissolve upon acidic or alkaline treatment. Alternatively, the first polysaccharide can be converted, for example by chemical or enzymatic means, into a second polysaccharide that is water soluble and/or will melt or dissolve upon acidic or alkaline treatment. Examples of products of the invention include bio-fuel, preferably ethanol or butanol, wood, paper, textile and yarn products.

A polysaccharide of the invention that can melt or dissolve upon acidic or alkaline treatment can be distinguished from other polysaccharides based on the random structure it forms when the polysaccharide units hydrogen bond to the each other. The polysaccharide can either be secreted or produced in the course of cell wall development and can intercalate between the cellulose fibers. The plant and its cell wall can then more easily absorb liquids such as solvents or enzymes and therefore make the processing of products of the invention, such as wood or paper products, cheaper and quicker. Moreover, the plant can be treated with a solution containing either an alkaline or acid, resulting in cell walls that are more amenable for the processing of products, such as the processing of plants into bio-fuels such as ethanol or butanol.

Examples of such polysaccharides include hyaluronan, fructan, curdlan and chitosan. By contrast, other polysaccharides form crystal type structures. Examples of such polysaccharides include, for example, cellulose and chitin. Accordingly, the plant of the invention is more receptive to liquid penetration than the wild type of plant.

According to specific embodiments of the invention, the enzyme is hyaluronan synthase and the polysaccharide is hyaluronan; the enzyme is a fructan synthase, preferably, levansucrase, and the polysaccharide is fructan; the enzyme is curdlan synthase and the polysaccharide is curdlan; or the enzyme is chitin deacetylase and the first polysaccharide is chitosan. Even more particularly, the enzymes include or consist of SEQ ID NOS:1 to 5.

As discussed above, alternatively, the first polysaccharide can be converted, for example by chemical means, into a second polysaccharide that will melt or dissolve upon acidic or alkaline treatment. For example, over-expression of an enzyme such as chitin synthase can cause chitin to be made. Chitin synthase can synthesize chitin. However, chitin is water insoluble. The enzyme chitin deacetylase can convert the chitin into chitosan which is soluble in dilute acid. Alternatively, the chitin can be converted into chitosan by heating in strong alkaline solution, for example sodium hydroxide, (>40%) at high temperature (90-120° C.).

Preferably, the enzyme of the invention can be over-expressed using a promoter. In a specific embodiment, the promoter is a constitutive plant promoter. In a more specific embodiment, the plant promoter is the CaMV 35S promoter. In another specific embodiment, the promoter is a tissue specific plant promoter. In a more specific embodiment, the plant promoter is the elongating tissue specific cell promoter. In another specific embodiment, the plant promoter is a development-specific promoter such as a fiber specific or xylem specific promoter. Examples of other such promoters are 4Cl and Cell.

Preferably, the over-expression and polysaccharide synthesis occurs in the cell wall of the plant. Accordingly, the enzyme of the invention can be over-expressed also using a sequence encoding a signal peptide. See, for example, U.S. Pat. No. 6,184,440. Preferably, the enzyme is a fructan synthase such as levansucrase.

In another embodiment, the present invention provides a transgenic plant over-expressing a nucleic acid molecule encoding an enzyme that catalyzes the synthesis of a polysaccharide that is in the cell wall and melts or dissolves upon acidic or alkaline treatment. In one aspect, it is provided that the enzyme is not hyaluronan synthase and the polysaccharide is not hyaluronan. In another aspect, the nucleic acid molecule or construct also encodes a signal peptide that directs over-expression in the cell wall. Accordingly and preferably, the enzyme is over-expressed in the cell wall. As explained above, the resulting transgenic plant is more receptive to liquid penetration than the wild type.

According to specific embodiments of the invention, the enzyme is a fructan synthase, preferably, levansucrase, and the polysaccharide is fructan; the enzyme is curdlan synthase and the polysaccharide is curdlan; or the enzyme is chitin synthase together with chitin deacetylase and the first polysaccharide is chitin and the second is chitosan.

Alternatively, the present invention involves modifying cellulose in order to make it more water soluble and/or more amenable for it and the plant it is within for processing. More specifically, cellulose microfibrils are insoluble cable-like structures that are typically composed of approximately 36 hydrogen-bonded chains containing 500 to 14,000 $\beta$-1,4-linked glucose molecules. Cellulose microfibrils comprise the core component of the cell walls that surround each cell. Roughly one-third of the total mass of many plants is cellulose. Somerville C., Annu. Rev. Cell Dev. Biol, 22:53-78 (2006).

The extended nature of the $\beta$-1,4-glucan chain creates a situation in which chains can interact with each other in a very precise manner to form a rigid structure. Thus, cellulose in nature never occurs as a single chain but packed from the time of synthesis as a crystal of many chains, called micro fibrils. The chains associate very strongly via both intra- and inter-chain hydrogen bonding between glucose residues in a manner so precise that microfibrillar cellulose is largely crystalline.

Structurally related polysaccharides, such as chitin and chitosan, are also found in the biosphere. Chitin, discussed above, is a $\beta$-1,4-linked homopolymer of N-acetylglucosamine. It is the second most abundant polymer in nature, after cellulose. Chitin is found in the exoskeleton of arthropods, in the cell wall of fungi, and in various components of diverse invertebrates. Chitin is difficult to process because of the large amounts of strong interchain hydrogen bonds. Chitosan, also discussed above, is partially or fully deacetylated chitin.

The present invention also encompasses an enzyme that leads to the incorporation of one or more units of N-acetylglucosamine or glucosamine into cellulose and, therefore, leads to the creation of polymers that are less crystalline and more water soluble than the micorfibrillar cellulose that is naturally found in the plant cell wall. The resulting cellulose-chitin or cellulose-chitosan polymers are incorporated into the cell wall and make the plant more amenable to processing.

An example of such an enzyme is glutamine:fructose 6-phosphate amidotransferase (GFAT, also known as glucosamine synthase), converts fructose-6-phosphate into glucosamine-6-phosphate, an intermediate in the UDP-N-acetylglucosamine metabolic pathway. The transformation of a plant with GFAT therefore leads the plant to produce N-acetylglucosamine in excess. cellulose synthase, which is naturally present in the plant, can then incorporate glucosamine and N-acetylglucosamine, while it is in excess, into the cellulose polymer for the creation of new amorphous glucose:N-acetylglucosamine and glucose:glucosamine copolymers (also referred to herein as cellulose-chitin and cellulose-chitosan, respectively).

The advantage of this aspect of the invention is to introduce a minimal change in the cell wall of the plant, where cellulose fibers are predominant, as discussed above. Accordingly, minimal change is made to the plant's phenotype, while still making it more water soluble and, therefore, more amenable to processing.

Indeed, control of the level of glucosamine or N-acetylglucosamine incorporated into cellulose provides new options in tailorability in terms of solubility and reactivity. Cellulose with water soluble glucosamine content can become soluble in dilute acid, leading to new processing options while maintaining cellulose-like properties, in contrast to cellulose, which has severe processing limitations due to low solubility in most solvents. Examples of glucose:N-acetylglucosamine copolymer molar ratios are 0.5 to 1.0 to 1.0 and, preferably, 0.8:1.0.

More particularly, glutamine:fructose 6-phosphate amidotransferase (GFAT, also known as glucosamine synthase) converts fructose-6-phosphate into glucosamine-6-phosphate, an intermediate in the UDP-N-acetylglucosamine metabolic pathway. Endosperm specific over-expression of plant GFAT fused to plastid signal peptide to target the enzyme into the plastid for the synthesis of cationic starch in transgenic corn has been described. See WO/2000/011192. Increased amounts of UDP-glucosamine could be detected in flour from endosperm of the transgenic corn. Expression of GFAT has also increased synthesis of hyaluronan in transgenic plants. WO/2007/039314.

All chloroviruses studied so far contained a functional gene for GFAT that produced the sugar precursor GlcNAc-6P required for chitin synthesis (Landstein et al., 1998). CVK2, a chitin producer type of chlorovirus encodes gfat gene (Acc no. AB107976) which encodes 596 aa protein (Swiss-Prot Q76DQ7). This makes CVK2 chitin production more efficient and abundant.

Chitosan is produced from chitin via a harsh thermochemical procedure. Temperature and NaOH concentration dramatically affect the rate of deacetylation. The optimal conditions for deacetylation of chitin are described in Chang et al., Carbohydrate Research 303:327-332 (1997). The use of chitin deacetylase (CDA) for the preparation of chitosan polymers and oligomers offers an enzymatic process that is much less harsh. CDA catalyses the hydrolysis of N-acetamido bonds in chitin to produce chitosan. Chitin deacetylases have been purified and characterized from several fungi, including *Mucor rouxii* (U.S. Pat. No. 5,525,502), *Absidia coerulea, Aspergillus nidulans* and two strains of *Colletotrichum lindemuthianum* (U.S. Pat. No. 6,057,144). Enzymes from *C. lindemuthianum* and *A. nidulans* not only have greater thermal stability, they are not inhibited by acetate, a product of the deacetylation reaction.

*C. lindemuthianum* UPS9 contain an ORF of 806 bp (Acc no. AY633657) encoding a preprotein (248 amino acids) with a signal peptide (27 amino acids) and an intron of 62 bp. Shrestha et al., Protein Exp. Purif., 38:196-204 (2004).

The GFAT gene can be cloned from the CVK2 virus and the CDA gene can be cloned from *C. lindemuthianum* UPS9. Over-expression of GFAT or the GFAT and CDA together in tobacco and poplar plants can be under the Cell promoter, which shows specific expression in growing cells, the 4CL-1 promoter, which shows specific expression in the secondary cell wall and the 35S promoter, which has strong constitutive expression. CDA can be fused to cell signal peptide to ensure deacetylation in the cell wall.

Over production of UDP-N-acetlyglucosamine allows incorporation of the subunit into cellulose polymers by cellulose synthases to produce the cellulose:chitin copolymer. The cellulose:chitin copolymer can be modified to cellulose:chitosan by NaOH treatment or by the CDA gene in-vivo when the two genes are over-expressed together in the transgenic plant, as discussed above.

In another aspect, the transgene of the subject invention can be an enzyme that can make an existing polymer in the plant, more specifically and preferably in the cell wall, more water soluble. An example of such an enzyme is cellobiose dehydrogenase (CDH) and an example of the existing polymer is cellulose. CDH can make cellulose polymers more water soluble than their natural forms.

CDH displays the properties of a typical dehydrogenase enzyme with oxidative and reductive half reactions that can be studied separately. The oxidative half reaction represents an oxidation in the C1 position of a saccharide. The hemiacetal at this position is converted to a lactone that hydrolyzes spontaneously to a carboxylic acid, cellobionic acid. Henriksson et al., J Biotechnol 78 93-113 (2000).

CDH can enhance cellulose degradation by cellulases. For example, it has been shown that the hydrolysis of microcrystalline cellulose by the cellulases of *T. reesei* is increased by the addition of CDH from *P. chrysosporium*. Bao and Renganathan, FEBS Lett. 302 77-80 (1992). CDH supplemented samples hydrolyzed 19% more cellulose than those without added CDH. The effects decreased as higher concentrations of CDH were used. The ability of CDH to bind to cellulose and to catalyze the formation of both $H_2O_2$ and $Fe^{2+}$ needed for hydroxyl radical production suggests that CDH disrupts the microcrystalline lattice of the cellulose and thus augments the fungal cellulases.

Another way that CDH can enhance cellulose degradation is elimination of the cellobiose product inhibition on the cellulases. Cellobionolactone, the product of cellobiose oxidation by CDH, does not inhibit the cellulases. Cameron and Aust, Arch. Biochem. Biophys. 376115-121 (1999). The reducing ends of cellulose may be able to repolymerize, or "snapback," with the non-reducing end of adjacent cellulose chains. CDH can catalyze reduction of electron acceptors using microcrystalline cellulose as the electron donor and thus CDH can probably oxidize the reducing ends of crystalline cellulose preventing repolymerization.

CDH can be obtained, for example, from the basidiomycete *P. chrysosporium*, in which under cellulolytic conditions this oxidoreductase represents about 0.5% of the extracellular protein. Raices et al., Biochem. Biophys. Acta 1576, 15-22 (2002). *P. chrysporium* contains 2.4-kb ORF encoding CDH (Acc no. x88897). As a secreted enzyme, CDH possess an 18 amino acid signal peptide sequence. The mature protein contains 755-amino-acids with a predicted mass of 80,115 Da (SwissProt Q12661). Sequence analysis suggests that the heme domain is located at the N terminus and that the flavin domain is located at the C terminus. CDH binds to cellulose similarly to cellulases.

CDH from *p. chrysporium* has been used for bleaching in the pulp and paper industry. Release of lignin occurs during bleaching. CDH has been found to be important for lignin degradation as it reduces phenoxy radicals and quinones formed by the action of phenol oxidases on degradation products from lignin. U.S. Pat. No. 5,866,392.

Products that include material from the transgenic plant of the invention include bio-fuel, particularly ethanol or butanol, wood, paper, textile and yarn products. Preferably, the enzyme of the invention can be over-expressed using a promoter. Examples of such promoters are 35S, 4Cl or Cell. Preferably, the over-expression and polysaccharide synthesis occurs in the cell wall of the plant. Accordingly, the enzyme of the invention can be over-expressed also using a sequence encoding a signal peptide. See, for example, U.S. Pat. No. 6,184,440. Preferably, the enzyme is a fructan synthase such as levansucrase.

The present invention also contemplates methods of making the products and transgenic plants disclosed above. Methods of making the plants include over-expressing a nucleic acid molecule encoding an enzyme that catalyzes the synthesis of a polysaccharide that is in the cell wall and melts or dissolves upon acidic treatment, provided that the enzyme is not hyaluronan synthase and the polysaccharide is not hyaluronan.

Regarding making bio-fuel products such as ethanol, in the biomass-to-ethanol processes the most energetic consuming step is the pretreatment. This process converts, by hydrolysis reactions, most of the hemicellulose portion of the feedstock to soluble sugars, primarily xylose, mannose, arabinose, and galactose. A small portion of the cellulose is converted to glucose. This conversion is accomplished using dilute sulfuric acid and high temperature (around 190° C.). These conditions allow some of the lignin to become soluble in the feedstock and "expose" the cellulose for subsequent enzymatic hydrolysis. From that point, cellulose can undergo saccharification and fermentation converting cellulose to ethanol or butanol. At the end, the amount of ethanol generated can be compared to that generated from the wild type plant material at the same industrial conditions.

Regarding making wood or paper products, in pulp making the first step is digestion which removes some of the lignin. The following step is bleaching that oxidizes the remaining lignin. If the cell-walls of the plant material is porous, as disclosed herein, more lignin will be removed in the digestion stage and therefore less chemicals will be needed in the bleaching step.

In addition, approximately 84% of wood pulping is generated by chemical processes. A first type of chemical pulping is called the kraft/soda process. This process uses a sodium-based alkaline solution (white liquor) consisting of sodium hydroxide and sodium sulfide, to digest the wood chips and produce pulp. A second type of chemical pulping is a sulfite process. In this process, an acidic solution of sulfurous acid and bisulfate ion is used to degrade the lignin. See Smook, In: *Handbook for pulp and paper technologists* (1992), 2nd ed. Wilde, Vancouver. The present invention makes either process cheaper and faster by making the cell walls more receptive to liquid absorption and disassembly. The degree of success can be measured by comparing performing the same process with a plant of the invention and the corresponding wild type, comparing, for example, the degree of liquid penetration of treatment or the speed or cost of creating the wood product.

Enzymes within the scope of the invention have been over-expressed. See, for example, Ebskamp et al., *Nature Biotech,* 12:272-75 (1994); Sevenier et al., *Nature Biotech,* 843-46 (1998); U.S. App. Pub. No. 20060168690 and U.S. Pat. No. 5,908,975. However, such enzymes were not shown to be expressed in the cell wall, and the resulting polysaccharides were not shown to be found there. Moreover, as disclosed above, the present invention contemplates making the products of the invention that include material from transgenic plants. By contrast, any art teaching enzymes of the invention do not teach or suggest doing so for making the products of the invention.

The transformed plants or their progenies are screened for plants that express the desired protein, polypeptide or enzyme. Moreover, engineered plants exhibiting the desired altered structure or morphology can be used in plant breeding or directly in agricultural production or industrial applications. Plants having one altered enzyme, protein or polypeptide can be crossed with other altered plants engineered with alterations in other growth modulation enzymes, proteins or polypeptides to produce lines with even further enhanced altered structural morphology characteristics compared to the parents or progenitor plants.

The properties of the nucleic acid sequences are varied as are the genetic structures of various potential host plant cells. This description of exemplary embodiments of the present invention includes a number of features which an artisan may recognize as not being absolutely essential, but clearly advantageous. These include methods of isolation, synthesis or construction of gene constructs, the manipulations of the gene constructs to be introduced into plant cells, certain features of the gene constructs, and certain features of the vectors associated with the gene constructs.

Further, the gene constructs of the present invention may be encoded on DNA or RNA molecules. According to the present invention, it is preferred that the desired, stable genotypic change of the target plant be effected through genomic integration of exogenously introduced nucleic acid construct(s), particularly recombinant DNA constructs. Nonetheless, according to the present invention, such genotypic changes can also be effected by the introduction of episomes (DNA or RNA) that can replicate autonomously and that are somatically and germinally stable. Where the introduced nucleic acid constructs comprise RNA, plant transformation or gene expression from such constructs may proceed through a DNA intermediate produced by reverse transcription.

The nucleic acid constructs described herein can be produced using methods well known to those skilled in the art. Artisans can refer to sources like Sambrook et al., 1989, Molecular Cloning: A Laboratory Manual, Cold Spring Harbor Laboratory Press, New York for teachings of recombinant DNA methods that can be used to isolate, characterize, and manipulate the components of the constructs as well as to build the constructs themselves. In some instances, where the nucleic acid sequence of a desired component is known, it may be advantageous to synthesize it rather than isolating it from a biological source. In other instances, the desired components may be advantageously produced by polymerase chain reaction (PCR) amplification.

In accord with the present invention, a transgenic plant with the ability to express an enzyme of the invention may be engineered by transforming a plant cell with a gene construct comprising a sequence encoding such an enzyme. In one embodiment, a plant promoter is operably associated with a sequence encoding the desired enzyme. "Operably associated" or "operably linked" is used herein to mean that transcription controlled by the "associated" or "operably linked" promoter produces a functional messenger RNA, whose translation produces the enzyme.

In a preferred embodiment of the present invention, the associated promoter is a strong and non tissue- or developmental-specific plant promoter (e.g., a promoter that strongly expresses in many or all plant tissue types). Examples of such strong, "constitutive" promoters include, but are not limited to, the CaMV 35S promoter, the T-DNA mannopine synthetase promoter, and their various derivatives.

In another embodiment of the present invention, it may be advantageous to engineer a plant with a gene construct comprising a sequence encoding an enzyme operably associated with a tissue- or developmental-specific promoter, such as, but not limited to the cell promoter, the CHS promoter, the PATATIN promoter and the 4Cl promoter. For example, where expression in elongating tissues and organs is desired, promoters such as the cell promoter may be used.

In yet another embodiment of the present invention, it may be advantageous to transform a plant with a gene construct comprising a sequence encoding an enzyme operably linked to a modified or artificial promoter. Typically, such promoters, constructed by recombining structural elements of different promoters, have unique expression patterns and/or levels not found in natural promoters. See e.g., Salina et al., *Plant Cell*, 4:1485-93 (1992), for examples of artificial promoters constructed from combining cis-regulatory elements with a promoter core.

In yet an additional embodiment of the present invention, the expression of gene encoding an enzyme of the invention may be engineered by increasing the copy number of the gene. One approach to producing a plant cell with increased copies of the desired gene is to transform with nucleic acid constructs that contain multiple copies of the gene. Alternatively, a gene encoding the desired polypeptide can be placed in a nucleic acid construct containing an amplification-selectable marker (ASM) gene such as the glutamine synthetase (GS) or dihydrofolate reductase gene. Cells transformed with such constructs are subjected to culturing regimes that select cell lines with increased copies of ASM gene. See, for example, Donn et al., *J. Mol. Appl. Genet.*, 2:549-62 (1984), for a selection protocol used to isolate of a plant cell line containing amplified copies of the GS gene. Because the desired gene is closely linked to the ASM gene, cell lines that amplified the ASM gene would also likely to have amplified the gene encoding the desired enzyme.

In still another embodiment of the present invention, the expression of the enzyme may be engineered by transforming a plant cell with a nucleic acid construct encoding a regulatory gene that controls the expression of the endogenous gene or a transgene encoding the desired enzyme, wherein the introduced regulatory gene is modified to allow for strong expression of the enzyme in the desired tissues and/or developmental stages.

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding .beta.-glucuronidase (Jefferson, *Plant Molec Biol. Rep*, 5:387-405 (1987)), luciferase (Ow et al., *Science*, 234:856-59 (1986)), and the B and C1 gene products that regulate anthocyanin pigment production (Goff et al., *EMBO J*, 9:2517-22 (1990)).

In embodiments of the present invention which utilize the Agrobacterium system for transforming plants (see infra), the recombinant DNA constructs additionally comprise at least the right T-DNA border sequence flanking the DNA sequences to be transformed into plant cell. In preferred embodiments, the sequences to be transferred in flanked by the right and left T-DNA border sequences. The proper design and construction of such T-DNA based transformation vectors are well known to those skilled in the art.

According to the present invention, a desirable plant may be obtained by transforming a plant cell with a nucleic acid construct described herein. In some instances, it may be desirable to engineer a plant or plant cell with several different gene constructs. Such engineering may be accomplished by transforming a plant or plant cell with all of the desired gene constructs simultaneously. Alternatively, the engineering may be carried out sequentially. That is, genetic engineering is accomplished by transforming with one gene construct, obtaining the desired transformant after selection and screening, transforming the transformant with a second gene construct, and so on. In certain embodiments, each gene construct can be linked to a different selectable or screenable marker gene so as to facilitate the identification of plant transformants containing multiple gene inserts. In other embodiment, several different genes may be incorporated into one plant by crossing parental lines engineered for each gene.

In an embodiment of the present invention, Agrobacterium is employed to introduce the gene construct into plants. Such transformation preferably uses binary Agrobacterium T-DNA vectors (Bevan, *Nuc. Acid Res.*, 12:8711-21 (1984)), and the co-cultivation procedure (Horsch et al., *Science*, 227:1229-31 (1985)). Generally, the Agrobacterium transformation system is used to engineer dicotyledonous plants (Bevan et al., 1982, *Ann. Rev. Genet* 16:357-384; Rogers et al., 1986, Methods Enzymol. 118:627-641). The Agrobacterium transformation system may also be used to transform, as well as transfer, DNA to monocotyledonous plants and plant cells (see Hernalsteen et al., *EMBO J*, 3:3039-41 (1984); Hooykass-Van Slogteren et al., *Nature*, 311:763-64 (1984); Grimsley et al., *Nature*, 325:1677-79 (1987); Boulton et al., *Plant Mol. Biol.*, 12:31-40 (1989); and Gould et al., *Plant Physiol.*, 95:426-434 (1991)).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, protoplast transformation through calcium-, polyethylene glycol (PEG)- or electroporation-mediated uptake of naked DNA (see Paszkowski et al., *EMBO J,* 3:2717-22 (1984), Potrykus et al., *Molec. Gen. Genet.,* 199:169-77 (1985); Fromm et al., *Proc. Nat. Acad. Sci. USA,* 82:5824-28 (1985); and Shimamoto, *Nature,* 338:274-76 (1989); and electroporation of plant tissues (D'Halluin et al., *Plant Cell,* 4:1495-1505 (1992)). Additional methods for plant cell transformation include microinjection, silicon carbide mediated DNA uptake (Kaeppler et al., *Plant Cell Reporter,* 9:415-418 (1990)), and microprojectile bombardment (see Klein et al., *Proc. Nat. Acad. Sci. USA,* 85:4305-09 (1983); and Gordon-Kamm et al., *Plant Cell,* 2:603-18 (1990)).

According to the present invention, a wide variety of plants and plant cell systems may be engineered for the desired physiological and agronomic characteristics described herein using the nucleic acid constructs of the present invention and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley, soybean), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), woody plants, conifers and pine trees (e.g., pine fir, loblolly pine, radiate pine, spruce); poplar, willow, eucalyptus, acacia, oil palm, sugar cane, Jerusalem artichoke; perennial grasses (e.g., switch grass, miscanthus); plants used in phytoremediation (e.g., heavy metal accumulating plants); oil crops (e.g., sunflower, rape seed) and plants used for experimental purposes (e.g., Arabidopsis).

As another example, DNA can be prepared from a transgenic plant, a DNA-specific primer is designed, and PCR is then carried out. After PCR has been carried out, the amplification product is subjected to agarose gel electrophoresis, polyacrylamide gel electrophoresis, or capillary electrophoresis and stained with ethidium bromide, a SYBR Green solution, or the like, thereby detecting the amplification product as a band. Thus, transformation can be confirmed. Alternatively, the amplification product can be detected via PCR with the use of a primer that has been previously labeled with a fluorescent dye or the like. Further, the amplification product may be bound to a solid phase such as a microplate to thereby confirm the amplification product via, for example, fluorescent or enzyme reactions.

As discussed above, monocotyledonous plants or dicotyledonous plants may be used for transformation. Examples of monocotyledonous plants include those belonging to: Graniineae such as rice, barley, wheat, maize, sugarcane, Zoysia, sorghum, Italian millet, and Japanese millet; Liliaceae such as asparagus, lily, onion, *Allium tuberosum*, and Japanese dogtooth violet; and Zingiberaceae such as ginger, *Zingiber mioga*, and *Curcuma longa*. Examples of dicotyledonous plants include, but are not limited to, those belonging to: Brassicaceae such as *Arabidopsis thaliana*, cabbage, rapeseed, cauliflower, broccoli, and radish; Solanaceae such as tomato, eggplant, potato, and tobacco; Leguminosae such as soybean, garden pea, kidney bean, and alfalfa; Cucurbitaceae such as cucumber, melon, and pumpkin; Umbelliferae such as carrot, celery, and *Cryptotaenia japonica*; Asteraceae such as lettuce; Malvaceae such as cotton and okra; Chenopodiaceae such as sugar beet and spinach; Myrtaceae such as Eucalyptus and clove; and Salicaceae such as poplar.

In the present invention, examples of plant materials to be transformed include: plant tissues such as a root, stem, leaf, seed, embryo, ovule, ovary, shoot apex (the growing point at the edge of a plant seedling), anther, and pollen; sections of such plant tissues; undifferentiated calluses; and cultured plant cells such as protoplasts prepared by removing cell walls via enzyme processing.

A transgenic plant in the present invention refers to a whole plant, a plant organ (such as a root, stem, leaf, petal, seed, or fruit), a plant tissue (such as the epidermis, phloem, parenchyma tissue, xylem, vascular bundle, palisade tissue, or spongy tissue), or a cultured plant cell.

When a cultured plant cell is to be transformed, an organ or individual may be re-generated from the obtained transformed cell via conventional tissue culture techniques. A person skilled in the art can easily carry out such procedures via a common technique that is known as a method of regenerating a plant from a plant cell. For example, a plant can be regenerated from a plant cell in the following manner.

When plant tissues or protoplasts are used as plant materials to be transformed, they are first cultured in a callus-forming medium that has been sterilized with the addition of, for example, inorganic elements, vitamins, carbon sources, saccharides as energy sources, or plant growth regulators (phytohormones, such as auxin or cytokinin), and indeterminately proliferating dedifferentiated calluses are allowed to form (hereafter, this process is referred to as "callus induction"). The thus formed calluses are transferred to a new medium containing plant growth regulators, such as auxin, and then further proliferated (i.e., subculture).

Callus induction is carried out in a solid medium such as agar, and subculture is carried out in, for example, a liquid medium. This enables both cultures to be carried out efficiently and in large quantities. Subsequently, the calluses proliferated via the aforementioned subculture are cultured under adequate conditions to induce redifferentiation of organs (hereafter referred to as "induction of redifferentiation"), and a complete plant is finally regenerated. Induction of redifferentiation can be carried out by adequately determining the type and quantity of each ingredient in the medium, such as plant growth regulators such as auxin or cytokinin, and carbon sources, light, temperature, and other conditions. Such induction of redifferentiation results in formation of adventitious embryos, adventitious roots, adventitious buds, adventitious shoots, and the like, which leads to growth into complete plants. Alternatively, such items may be stored in a state that pertains before they become complete plants (e.g., encapsulated artificial seeds, dry embryos, or freeze-dried cells and tissues).

According to the present invention, desired plants may be obtained by engineering one or more of the disclosed gene constructs into a variety of plant cell types, including but not limited to, protoplasts, tissue culture cells, tissue and organ explants, pollens, embryos as well as whole plants. In an embodiment of the present invention, the engineered plant material is selected or screened for transformants (those that have incorporated or integrated the introduced gene construct(s)) following the approaches and methods described below. An isolated transformant may then be regenerated into a plant. Alternatively, the engineered plant material may be regenerated into a plant or plantlet before subjecting the derived plant or plantlet to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the .beta.-glucuronidase, luciferase, B or C1 genes) that may be present on the recombinant nucleic acid constructs of the present invention. Such selection and screening methodologies are well known to those skilled in the art.

Physical and biochemical methods also may be used to identify plant or plant cell transformants containing the gene constructs of the present invention. These methods include but are not limited to: 1) Southern analysis or PCR amplification for detecting and determining the structure of the recombinant DNA insert; 2) Northern blot, Real-time quantitative RT-PCR, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immuno-staining, also may be used to detect the presence or expression of the recombinant construct in specific plant organs and tissues. The methods for doing all these assays are well known to those skilled in the art.

The gene of the present invention can be introduced into a plant and then used as a selection marker gene for a transgenic plant. The marker gene of the present invention may be introduced alone or in combination with the other target gene to be expressed.

The marker gene of the present invention may be introduced into a monocotyledonous or dicotyledonous plant. Examples thereof are as listed above, and plants capable of callus formation are preferable.

The marker gene of the present invention can be introduced into, for example; plant tissues such as a root, stem, leaf, seed, embryo, ovule, ovary, shoot apex (the growing point at the edge of a plant seedling), anther, and pollen; sections of such plant tissues; undifferentiated calluses; and cultured plant cells such as protoplasts prepared by removing cell walls via enzyme processing. In the present invention, the marker gene is generally introduced into a tissue section, callus, or protoplast removed from the plant for the purpose of introduction of such gene into the plant, and the introduced marker gene is incorporated in the cell of the plant tissue, and particularly in its chromosome.

When the marker gene is introduced into a plant alone, the marker gene can be ligated to a plasmid to prepare a recombinant vector. When the marker gene is introduced into a plant together with the target gene, however, the marker gene and the target gene are ligated to the same plasmid to prepare a recombinant vector. Alternatively, a recombinant vector that is obtained by ligating the selection marker gene to a plasmid may be prepared separately from a recombinant vector that is obtained by ligating the target gene to a plasmid. When recombinant vectors are separately prepared, both vectors are co-transfected into a host. During vector preparation, a promoter can be ligated to a position upstream of the target gene or the marker gene, and the terminator can be ligated to a position downstream thereof. Examples of promoters include a cauliflower mosaic virus 35S promoter, OCS-mas super promoter, an actin promoter, and an ubiquitin promoter. An example of a terminator is a nopalin synthase gene terminator. Examples of the methods for introducing the vector into a plant include the aforementioned methods and methods similar thereto.

A gene that exhibits other properties, such as antimicrobial activities against given bacteria, tolerance to a given drug, the capacity for synthesizing a given useful material, sensitivity to a given phytohormone, or morphological properties different from those of the original plant, may be incorporated in the vector together with the marker gene of the present invention to obtain a re-differentiated plant exhibiting such properties.

It is preferable to form a callus from the protoplast or plant tissue into which the marker gene has been introduced in the aforementioned manner and to further culture the formed callus. Methods of callus induction, subculture, and induction of re-differentiation are as described above.

The selected plant may be allowed to grow in accordance with the aforementioned technique that is commonly adopted in plant tissue culturing. Alternatively, such items may be stored in a state that pertains before they become complete plants (e.g., encapsulated artificial seeds, dry embryos, or freeze-dried cells and tissues).

The present invention also encompass nucleic acid sequences that have at least 70%, 80%, 90%, 95%, 96%, 97%, 98% and 99% or more homology with SEQ ID NOS:1 to 5. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.*, 35:351-360 (1987). The method used is similar to the method described by Higgins & Sharp, *CABIOS*, 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.*, 12:387-395 (1984).

Another example of algorithm that is suitable for determining percent sequence identity and sequence similarity are the BLAST and BLAST 2.0 algorithms, which are described in Altschul et al., *Nuc. Acids Res*, 25:3389-3402 (1977) and Altschul et al., *J. Mol. Biol.*, 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The gene according to the present invention also includes DNA that hybridizes under stringent conditions to DNA consisting of the nucleotide sequence complementary to DNA consisting of the nucleotide sequence as shown in SEQ ID NOS:1 to 5. The present invention also includes DNA that hybridizes under stringent conditions to DNA consisting of the nucleotide sequence complementary to DNA comprising or consisting of SEQ ID NOS:1 to 5.

The term "stringent conditions" refers to conditions where what is called a specific hybrid is formed but a non-specific hybrid is not formed. Under such conditions, for example, complementary strands of DNA consisting of a highly homologous nucleic acid, i.e., DNA consisting of a nucleotide sequence exhibiting about 65% or higher, preferably about 75% or higher, more preferably about 85% or higher, and most preferably about 95% or higher, homology to the nucleotide sequence as shown in SEQ ID NOS:1 to 5 hybridize, but complementary strands of a nucleic acid having homology lower than the aforementioned level do not hybridize. More specific conditions are constituted by a sodium concentration of 150 mM to 900 mM, and preferably 600 mM to 900 mM, and a temperature of 60° C. to 68° C. and preferably 65° C.

An enzyme of the present invention can also include on more deletion, addition or substitutions of the encoded protein that would not eliminate its activity, as known by the skilled artisan. The deletion, addition, and substitution of amino acid residues can be carried out by modifying the aforementioned protein-encoding gene via a technique known in the art. Mutation can be introduced to a gene via conventional techniques such as the Kunkel method or the Gapped duplex method, or via a technique in accordance therewith. For example, mutation is introduced using a mutagenesis kit, such as a Mutant-K (Takara) or Mutant-G (Takara) utilizing site-directed mutagenesis or the Takara LA PCR in vitro Mutagenesis series kit (Takara).

Once the nucleotide sequence of the gene according to the present invention is determined, the gene according to the present invention can be then obtained via chemical synthesis, PCR utilizing the cloned cDNA as a template, or hybridization utilizing a DNA fragment having such nucleotide sequence as a probe. Further, modified DNA that encodes the aforementioned gene can be synthesized via, for example, site-directed mutagenesis.

The invention also relates to Cell derivatives or analogues made by altering the cell sequence by substitutions, additions or deletions that provide molecules with the enzymatic activity disclosed herein. Thus, the enzymes of the invention include polypeptides containing, as a primary amino acid sequence, all or part of the amino acid sequences encoded by SEQ ID NOS:1 to 5 including altered sequences in which functionally equivalent amino acid residues are substituted for residues within the sequence resulting in a polypeptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such enzymatic derivatives can be made either by chemical peptide synthesis or by recombinant production from nucleic acid encoding the enzyme which nucleic acid has been mutated. Any technique for mutagenesis known in the art can be used, including, but not limited to, chemical mutagenesis, in vitro site-directed mutagenesis, use of TAB® linkers (Pharmacia) and PCR with mutation-containing primers.

Furthermore, if desired, nonclassical amino acids or chemical amino acid analogues can be introduced as a substitution or addition into the enzyme, derivative or analogue. Non-classical amino acids include, but are not limited to, the D-isomers of the common amino acids, 2,4-diaminobutyric acid, .alpha.-amino isobutyric acid, 4-aminobutyric acid, Abu, 2-amino butyric acid, .gamma.-Abu, .epsilon.-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, .beta.-alanine, fluoro-amino acids, designer amino acids such as .beta.-methyl amino acids, C.alpha.-methyl amino acids, N.alpha.-methyl amino acids, and amino acid analogues in general. Furthermore, the amino acid can be D (dextrorotary) or L (levorotary).

The invention also relates to isolated nucleic acid molecules which comprise the nucleotide sequence of the promoter. The invention also encompasses (a) recombinant nucleic acid vectors that contain any of the foregoing plant coding sequences and/or their complements (i.e., antisense); (b) recombinant nucleic acid expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the promoters derived from the genome of plant cells (e.g., heat shock promoters; the promoter for the small subunit of RUBISCO; the promoter for the chlorophyll a/b binding protein) or from plant viruses (e.g., the 355 RNA promoter of CaMV; the coat protein promoter of tobacco mosaic virus (TMV), cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast .alpha.-mating factors.

The present invention encompasses a recombinant nucleic acid vector comprising the nucleic acid molecule comprising (a) SEQ ID NOS:1 to 5; (b) variant nucleotide sequences of SEQ ID NOS:1 to 5 which is an allelic variant, species variant, and naturally occurring or man-made functional variants thereof; or (c) a nucleic acid molecule encoding derivatives or analogs of a polypeptide encoded by SEQ ID NOS:1 to 5.

The invention also relates to host cells containing the recombinant nucleic acid vectors described above. The present invention further relates to recombinant nucleic acid vectors comprising a first nucleic acid sequence encoding a secretion signal peptide and a second nucleic acid sequence encoding an enzyme of the invention.

The invention also encompasses proteins that are functionally equivalent to the enzymes encoded by the SEQ ID NOS:1 to 5, as judged by any of a number of criteria, including but not limited the enzymatic activity disclosed herein. Such functionally equivalent enzymes include but are not limited to additions or substitutions of amino acid residues within the amino acid sequence encoded by the nucleotide sequences described above, but which result in a silent change, thus producing a functionally equivalent gene product.

Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to DNA (using random mutagenesis techniques well known to those skilled in the art) and the resulting mutant enzymes tested for activity, site-directed mutations of the coding sequence can be engineered (using site-directed mutagenesis techniques well known to those skilled in the art) to generate mutant plant cells with increased function.

Other mutations to the coding sequence can be made to generate enzymes that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites.

While the polypeptides can be chemically synthesized, large polypeptides itself may advantageously be produced by recombinant DNA technology using techniques well known in the art for expressing nucleic acid containing enzymatic gene sequences and/or coding sequences. Such methods can be used to construct expression vectors containing the nucleotide sequences described and appropriate transcriptional and translational control signals. These methods include, for example, in vitro recombinant DNA techniques, synthetic techniques, and in vivo genetic recombination. Alternatively, RNA capable of encoding cell nucleotide sequences may be chemically synthesized using, for example, synthesizers.

Also included within the scope of the invention are enzymatic proteins, derivatives, and analogues which are differentially modified during or after synthesis, e.g., by biotinylation, benzylation, glycosylation, acetylation, phosphorylation, amidation, pegylation, derivatization by known protecting/blocking groups, proteolytic cleavage, linkage to an antibody molecule or other cellular ligand. Any of numerous chemical modifications may be carried out by known techniques, including, but not limited to, acetylation, formylation, oxidation, reduction or metabolic synthesis in the presence of tunicamycin. These modifications may serve to increase the stability, bioavailability and/or action of the enzymes of the invention.

Any of the enzymes, derivatives or analogues described above may, additionally, have a non-peptide macromolecular carrier group covalently attached to its amino and/or carboxy termini. Such macromolecular carrier groups may include, for example, lipid-fatty acid conjugates or carbohydrates.

A variety of host-expression vector systems may be utilized to express the nucleotide sequences of the invention. Methods which are well known to those skilled in the art can be used to construct expression vectors containing the coding sequence and appropriate transcriptional/translational control signals. These methods include in vitro recombinant DNA techniques, synthetic techniques and in vivo recombination/genetic recombination.

A variety of host-expression vector systems may be utilized to express the coding sequence. These include but are not limited to microorganisms such as bacteria transformed with recombinant bacteriophage DNA, plasmid DNA or cosmid DNA expression vectors containing the plant GluR coding sequence; yeast transformed with recombinant yeast expression vectors containing the plant GluR coding sequence; insect systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems infected with recombinant virus expression vectors (e.g., adenovirus, vaccinia virus) including cell lines engineered to contain multiple copies of the sequence either stably amplified (CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage .lambda., plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., the cell promoter, heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of the cell DNA SV40-, BPV- and EBV-based vectors may be used with an appropriate selectable marker.

In cases where plant expression vectors are used, the expression of the coding sequence may be driven by any of a number of promoters. For example, viral promoters such as the 35S RNA and 19S RNA promoters of CaMV or the coat protein promoter of TMV may be used. Alternatively, plant promoters such as the cell promoter or functional fragments thereof, the small subunit of RUBISCO or heat shock promoters, e.g., soybean hsp17.5-E or hsp17.3-B, may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, *Methods for Plant Molecular Biology*, Academic Press, NY, Section VIII, pp. 421-463 (1988); and Grierson & Corey, *Plant Molecular Biology*, 2d Ed., Blackie, London, Ch. 7-9 (1988).

For long-term, high-yield production of recombinant proteins, stable expression is preferred. For example, cell lines which stably express the enzyme may be engineered. Rather than using expression vectors which contain viral origins of replication, host cells can be transformed with the enzyme DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase, hypoxanthine-guanine phosphoribosyltransferase and adenine phosphoribosyltransferase genes that can be employed in $tk^-$, $hgprt^-$ or $aprt^-$-cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin genes. Additional selectable genes have been described, namely trpB, which allows cells to utilize indole in place of tryptophan; hisD, which allows cells to utilize histinol in place of histidine; and ODC (ornithine decarboxylase) which confers resistance to the ornithine decarboxylase inhibitor, 2-(difluoromethyl)-DL-ornithine, DFMO. The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells and/or plants that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression.

EXAMPLES

The following examples are presented for purposes of illustration only and are not intended to limit the scope of the invention in any way.

Example 1

This example shows the synthesis of chitin and chitosan in plants and its effects.

Chitin, a β-1,4-linked homopolymer of N-acetyl-D-glucosamine (GlcNAc), is the second most abundant polymer in nature, after cellulose. Chitin is found in the exoskeleton of arthropods, in the cell wall of fungi, and in various components of diverse invertebrates (Kawasaki et al., *Virology:* 302, 123-31 (2002).

Chitosan is a partially or fully deacetylated chitin. It is naturally present in some microorganisms and fungi. The degree of deacetylation is varied from 40% to 98%. The soluble polysaccharide is positively charged. The solubility of chitosan depends on pH and the degree of deacetylation. It is well soluble in diluted acidic solutions. The viscosity of chitosan in solution is increased with increasing the degree of deacetylation and decreasing temperature Ilium L., *Pharm. Res.,* 15:1326-31 (1998).

Chlorovirus CVK2 has a gene for functional chitin synthase (CHS; Acc no. AB071039; SEQ ID NO:1) which encodes 516 aa protein (Swiss-Prot Q8V735). CVK2 CHS showed a high similarity to the CHS3-type enzymes of yeasts and fungi. However, its size is significantly smaller than fungal enzymes (1000-1300 a.a.), and the sequence homology is restricted to a carboxy-terminal region of those enzymes where the conserved catalytic site exists (Nagahashi et al., *J. Biol. Chem.,* 270:13961-67 (1995); Kawasaki et al., 2002, supra). The N-terminal regions extended in fungal enzymes are suggested to be involved in the processing and regulation of enzyme activities (Nagahashi et al., 1995, supra). The smaller size of the CVK2 CHS protein may reflect its simpler regulatory and processing mechanism as well as different localization processes in the cell. Newly synthesized chitin was efficiently secreted across the Chlorella membrane and cell wall to the extracellular matrix, suggesting that the CVK2 CHS protein may be integrated into the membrane and cell wall, where it synthesizes chitin molecules by the addition of UDP-GlcNAc and transports the insoluble material to the extracellular space (Cabib, E., *Adv. Enzymol. Relat. Areas Mol. Biol.* 59:59-101 (1987)). All chloroviruses along with the CVK2 studied so far contain a functional gene for GFAT that produced the sugar precursor GlcNAc-6P required for chitin synthesis (Landstein et al., *Virology,* 250: 388-96 (1998)). This functional gene makes CVK2 chitin production more efficient and abundant.

Methods of Chitin Deacetylation to Produce Chitosan

Chitosan is produced from chitin via a harsh thermochemical procedure. Temperature and NaOH concentration dramatically affect the rate of deacetylation. The optimal conditions for deacetylation of chitin are described in Chang et al., *Carbohydrate Research,* 303:327-32 (1997). The use of chitin deacetylase for the preparation of chitosan polymers and oligomers can overcome most of these drawbacks. Chitin deacetylase (CDA; EC 3.5.1.41) catalyses the hydrolysis of N-acetamido bonds in chitin to produce chitosan. Chitin deacetylases have been purified and characterized from several fungi. The well-studied enzymes are those from the fungi *Mucor rouxii* (U.S. Pat. No. 5,525,502), *Absidia coerulea, Aspergillus nidulans* and two strains of *Colletotrichum lindemuthianum* (U.S. Pat. No. 6,057,144). One interesting property with a potential biotechnological application for the enzymes from *C. lindemuthianum* and *A. nidulans* is that, apart from their thermal stability, they are not inhibited by acetate, a product of the deacetylation reaction (Tsigos et al., *Trends Biotechnol.,* 18:305-12 (2000)). *C. lindemuthianum* UPS9 contain an ORF of 806 bp (Acc no. AY633657; SEQ ID NO:2) encoding a preprotein (248 amino acids) with a signal peptide (27 amino acids) and an intron of 62 bp (Shrestha et al., *Protein Expr. Purif.,* 38:196-204 (2004)).

The CHS gene from CVK2 and the CDA gene from *C. lindemuthianum* UPS9 is cloned. The CHS gene alone or the two genes together are over-expressed in tobacco and poplar plants under Cell promoter (specific expression in growing cells), 4CL-1 promoter (specific expression in secondary cell wall) with and 35S promoter (strong constitutive expression).

Chitin is modified to chitosan by NaOH treatment in the mill or by the CDA gene in-vivo when the two genes are over-expressed together in the transgenic plant. Chitosan molecules melt or dissolve during the acidic treatment in the mill and facilitate the liquid penetration and cell wall disassembly.

Example 2

This example shows the synthesis of hyaluronic acid in plants and its effects.

Hyaluronan or hyaluronic acid (HA) is a variable length, long-chain polysaccharide containing repeating disaccharide units of glucuronic acid and n-acetylglucosamine. Long considered a relatively inert component of the extracellular matrix particularly of soft connective tissues in vertebrates, this polysaccharide displays intriguing viscoelastic and conformational features. HA is a highly hydrophilic biomolecule, behaving in aqueous solution as an expanded random coil of considerable intrinsic stiffness. HA is also coming under scrutiny as a potential therapeutic agent for a number of different diseases, based on its recently discovered role in modulating inflammation (DeAngelis, P. L, *Cell Mol. Life Sci.,* 56:670-82 (1999)).

HA synthases (HASs) are integral membrane proteins that polymerize the HA molecule using activated uridine diphosphate (UDP)-sugar nucleotides as substrates. Amino acid sequences for some HASs have been deduced from gene sequencing with sizes range from 419 to 588 residues (DeAngelis et al., *J. Biol. Chem.,* 268:19181-84 (1993)). Although numerous studies have been performed with respect to the importance of HA in a large number of biological and pathological processes, the enzymes responsible for its synthesis have been elusive until recently. The cloning of the streptococcal HA synthase (HAS) led to the identification of three mammalian enzymes referred to as HAS1, HAS2 and HAS3 (Recklies et al., *Biochem. J,* 354:17-24 (2001)). Recently it has been found that the chlorella virus PBCV-1 contain a ~1900 bp ORF A98R (GenBank acc no. U42580; SEQ ID NO:3), encoding a 568-residue protein with similarity to the known HASs (DeAngelis et al., *Science,* 278:1800-03 (1997)). Cloning and expression of recombinant A98R protein in plants and isolation of hyaluronic acid has been previously described (United States App. Pub. No. 20060168690).

Figure 9:
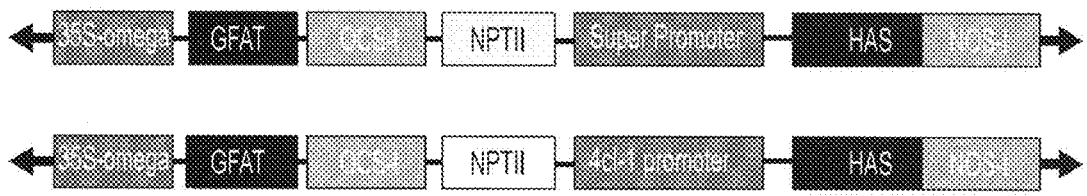
FIG. 9 shows the construct of chimeric hyaluronan synthase (has) under constitutive (super promoter) and secondary development (4cl-1) promoters and glutamine-fructose- 6-phosphate transaminase (GFAT) under constitutive promoter (35S with enhancer) used for tobacco plant transformation.

A. Preparation of Constructs:

Constructs containing different promoters that express the hyaluronan synthase gene at different stages of the plant cell wall development were prepared for the transformation of tobacco plants (*Nicotiana tabacum*). See FIG. 9.

B. Dilute Acid Pretreatment

Plant samples (200 mg dried tobacco stems) were mixed with 1.8 ml dilute sulfuric acid solution (1% wt/vol) in a glass Erlenmeyer and heated for 1 h in an autoclave set at 121° C. The solid pretreatment residues were enzymatically hydrolyzed.

C. Enzymatic Hydrolysis

A modified version of the NREL Laboratory analytical procedure 9 was used to determine cellulose digestibility. Brown L. and Torget R. Enzymatic saccharification of lignocellulosic biomass; LAP-009. NREL Analytical Procedure. National Renewable Energy Laboratory, Golden, Colo. Acid-pretreated samples were washes with DDW and filtered on glass filter paper and oven dried. Samples were buffered by adding 1.5 ml of 1M citric acid (pH 4.8), cellulase from trichoderme viride (1 ml) and thymol (15 µl of a 50 g l$^{-1}$ solution in 70% vol/vol ethanol) to reach a final volume of 15 ml. The contents were incubated for 72 h in a shaker incubator set at 45° C. and 125 rpm. The cellulase mixture had an activity of 40 filter paper units, ml$^{-1}$, as measured by the previously described procedure of Ghose. Incubation supernatants were analyzed for soluble carbohydrates. Total soluble carbohydrates were analyzed by DNS reagent according to Ghose. Ghose, T. K., Pure and Applied Chemistry 59:257-268 (1984).

D. Results

Figure 10A:
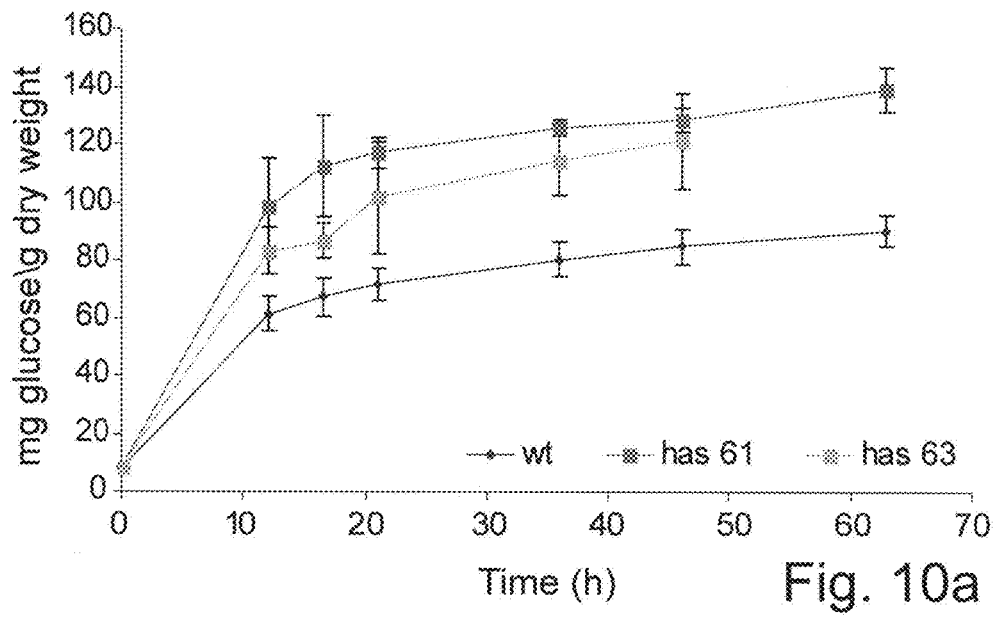
FIG. 10A compares the reducing sugars released by hydrolysis (mg\g dry weight) in different times (hours).
Figure 10B:
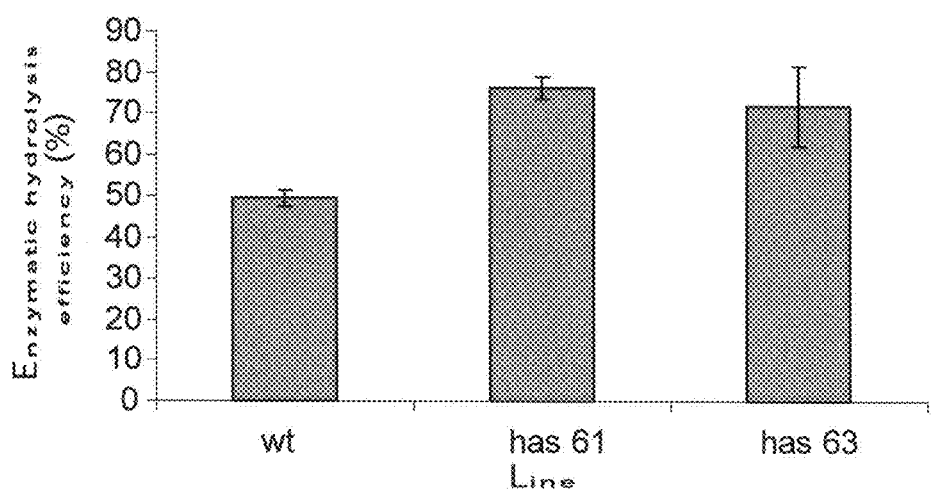
FIG. 10B compares the saccharification efficiency (total sugar released as a percentage of sugars released from filter paper) for biomass subjected to enzymatic hydrolysis with cellulase and acid pretreatment.

Saccharification efficiency and reducing sugars released (mg\g dry weight) of biomass of 2 independent hyaluronic acid synthase under 4cl-1 promoter transgenic lines (has61 and has63) are greater than that of control plants. See FIG. 10. After 72 h incubation, saccharification efficiency was 71-76% in has61 and has63 lines, compared to 49% in controls.

Example 3

This example shows the synthesis of curdlan in plants and its effects.

Curdlan is a high molecular weight polymer of glucose, β-1,3-glucan produced by pure culture fermentation from a non-pathogenic and non-toxicogenic strain of bacterium *Agrobacterium biobar* 1 (identified as *Alcaligenes faecalis* var. *myxogenes* at the time of discovery) or *Agrobacterium radiobactor*. Curdlan consists of β-(1,3)-linked glucose residues and has the unusual property of forming an elastic gel upon heating its aqueous suspension (McIntosh et al., *Appl. Microbiol. Biotechnol.*, 68:163-73 (2005)). Three forms of regenerated curdlan have been identified and the structural differences between them proposed. Kasai N. and Harada T., Fiber *Diffraction Methods*, ACS Symp. Ser. No. 141, Washington, D.C. 363-383 (French A. D. and Gardner K. H. eds. (1980).

Curdlan exists as a triple helix, single helix or single chain depending mainly on degree of hydration, heating temperature and solvent conditions (Zhang et al., *Int. J. Biol. Macromol.*, 30:7-16 (2002)). Heating aqueous suspensions of curdlan above 80° C. and then cooling it produces a high-set, thermo-irreversible gel, whereas a low-set, thermo-reversible gel is produced on heating to 55° C. Gelation involves aggregation of the rod-like triple helices through non-covalent associations (extended junction zones). At high temperatures, the triple-helical strands may unwind to give single chains that, as the temperature is lowered, anneal to reform triple helices. In high-set gels, single chains involved in more than one complex may interconnect the triple helices. In low-set gels, curdlan molecules are present as single helical chains (Kasai and Harada 1980, supra). In alkaline solutions, the curdlan triple helix unwinds and, on neutralization or dialysis against water, a low-set gel is formed without heating. Such neutralized gels are converted to irreversible high-set gels on heating to above 80° C. The rheological and thermal behavior of low- and high-set curdlan gels has been documented (Zhang et al. 2002, supra).

Curdlan synthase (crdS; acc no. AF057142; SEQ ID NO:4) product (73 kDa) deduced from the DNA sequence (1,965 bp) shares homology with beta-d-glycan synthases, including bacterial and plant cellulose synthases, and chito-oligosaccharide and hyaluronan synthases, which are members of glycosyltransferase family GT2 (Coutinho P. M. and Henrissat B., *Recent advances in carbohydrate bioengineering*, The Royal Society of Chemistry, (Cambridge Gilbert H J, Davies G, Henrissat B, Svensson B eds. (1999)). In Agrobacterium, CrdS is an integral inner membrane protein with seven transmembrane (TM) helices, one non-membrane-spanning amphipathic helix and a $N_{out}$–$C^{in}$ disposition (Karnezis et al., *Trends Glycosci Glycotechnol*, 12:211-27 (2000); Karnezis et al., *Glycobiology*, 13:693-706 (2003)).

The crdS gene is cloned from Agrobacterium sp. ATCC31749 and over-expressed the crdS in tobacco and poplar plants under Cell promoter (specific expression in growing cells), 4CL-1 promoter (specific expression in secondary cell wall) with and 35S promoter (strong constitutive expression).

Transgenic plant materials containing the curdlan molecule will form a gel during the heat treatment, melt or dissolve during the acidic treatment in the mill and will facilitate the liquid penetration and cell walls disassembly.

Example 4

This example shows the synthesis of fructan in plants and its effects.

Fructan (oligo- and poly-fructose) rather than starch occurs naturally as the primary reserve carbohydrate in 12-15% of higher plants. The most obvious differences between starch and fructan are the location and solubility. Fructans are located in the vacuole and are soluble, in contrast to the insoluble plastidic starch.

Fructan-producing bacteria can be found in a wide range of organisms, including plant pathogens and the bacteria present in oral and gut floras of animals and humans. Examples of bacterial genera in which fructan-producing strains can be found are *Bacillus, Streptococcus, Pseudomonas, Erwinia*, and *Actinomyces* (Hendry and Wallace, *Science and Technology of Fructans*, pp. 119-139 (CRC Press, Boca Raton, Fla., M Suzuki, N.J. Chatterton, eds, (1993). In general, bacteria produce fructan molecules consisting mainly of β-(2-6)-linked fructosyl residues, occasionally containing β-(2-1)-linked branches. Such fructans are called levans and can reach a DP of more than 100,000 fructose units. Bacterial levan is produced extracellularly by a single enzyme, levansucrase (LSC), which produces levan directly from sucrose (Vijn & Smeekens, Vijn I. and Smeekens S., *Plant Physiol.*, 120:351-59 (1999). *E. amylovora* contain an lsc gene (1248 bp; SEQ ID NO:5) that encode 415 aa protein (acc no. X75079).

Plants transformed with LSC have been shown to contain more high molecular weight fructans compared to wild type plants.

A. Levan Precipitation:

500 mg dry materials were ground with a mortar and pestle and the powder extracted with 2 ml of 80% boiling ethanol for 15 min. After centrifugation at 10,000 g for 10 min, the pellet was re-extracted three times with 1 ml water at 80° C. for 15 min each time. The extracts were pooled and concentrated to 50 μl in a Speed-Vac concentrator.

Figure 11:
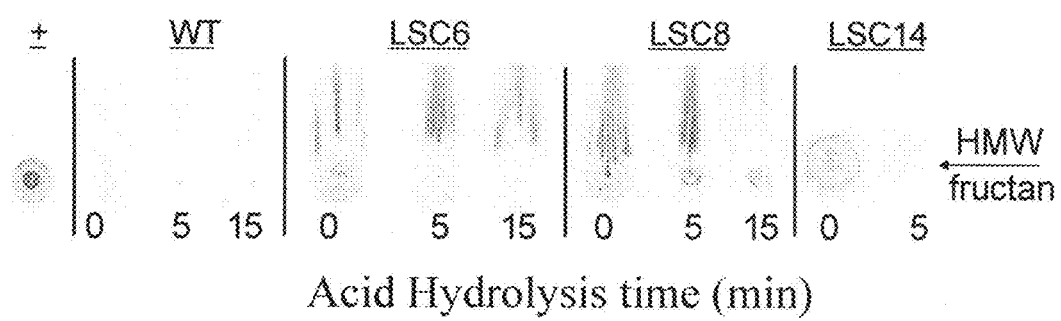
FIG. 11 shows the TLC analysis of HMW fructan accumulation in 3 independent lsc-transgenic tobacco plants. High molecular weight (HMW) fructan from *Helianthus tuberosus* was used as a positive control. Samples were subjected to acid-hydrolysis in different times.

B. TLC Analysis:

TLC analysis was performed in 10 cm×20 cm vertical trough glass developing chambers by the solvent vapour saturation. Prior to TLC analysis, silica gel layers were pretreated with 0.02 M sodium acetate. The plates were then dried at 50° C. in an oven for 5 min. 10 ul of samples were subjected to bottom of the plate. The layers were developed with ethanol-water (85:15, v/v) as mobile phase at laboratory temperature. After the layer developing and evaporating of mobile phase in a flow of warm air for 15 min, sugars were detected by the urea-phosphoric acid spray. Wise et al., Ann. Biochem. 27:33-36 (1955). Purified fructan from *Helianthus tuberosus* and fructose were used as standards. High molecular weight fructans in lsc-transgenic plants have been detected. FIG. 11.

Levansucrase catalyzes the synthesis of the water-soluble fructan polymer from sucrose. Expressing levansucrase in the cell wall will result in wood containing fructan polymers that intercalate into the normal cell wall. The generation of soluble "pockets" of fructan in the cell wall, will enable the rapid penetration of solvents and enzymes thus facilitating the more rapid and cheaper processing of wood in industrial processes. We report the expression of bacterial levansucrase in transgenic Eucalyptus plants under different promoters. The affects on plant growth and cell wall architecture is presented.

Figure 4:
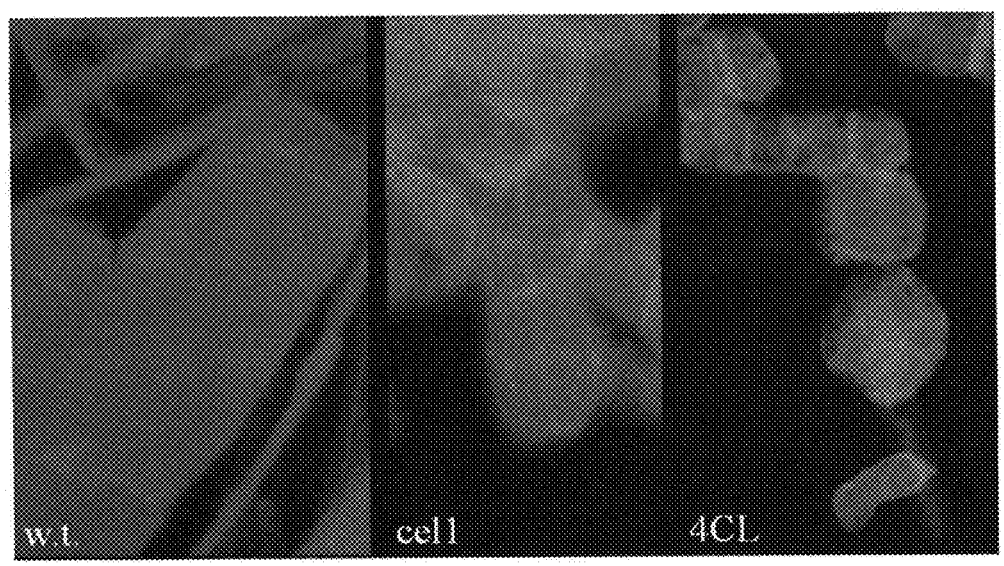
FIG. 4 shows UV light microscopy of plant cells with calcoflour staining: the cells were pre-incubated for 24 hours in acid-alcohol solution and ammonium oxalate to macerate tissue. The cell walls are highly porous compared with the wild type. Plants were grown in tissue culture for 5 weeks before treatment.

Constructs containing different promoters that express the Lsc gene at different stages of the plant cell wall development were prepared for Eucalyptus hybrid (*E. europhylla×E. grandis*) transformation. See FIG. 1. As shown in FIG. 2, a slightly higher percentage of transformation was achieved using the 4CL promoter compared to the cell promoter. As shown in FIG. 3, there was a significant difference in cell wall structure between wild type and the Lsc expressing transgenic plants. As shown in FIG. 4, the cells of transgenic plants are notably smaller compared to wild type. The cell walls are highly porous compared with the wild type.

The results described above show that 4CL-Lsc transgene did not cause any significant reduction in plant growth but resulted in a significantly porous cell wall phenotype. The Lsc gene is therefore an important addition for the genetic improvement of wood for industrial processing.

Expressing levansucrase in the cell wall is expected to result in wood containing fructan polymers that intercalate into the normal cell wall. The generation of soluble "pockets" of fructan in the cell wall will enable the rapid penetration of solvents and enzymes thus facilitating the more rapid and cheaper processing of wood in industrial processes.

All references cited herein are incorporated in their entirety. It is appreciated that the detailed description above is intended only to illustrate certain preferred embodiments of the present invention. It is in no way intended to limit the scope of the invention, as set out in the claims.

What is claimed is:

1. A transgenic plant expressing a nucleic acid sequence encoding a cellobiose dehydrogenase (CDH) polypeptide, wherein said polypeptide is expressed in the cell wall of the plant using a nucleic acid sequence encoding a signal peptide, wherein the cell wall of the transgenic plant is more water soluble than the cell wall of the wild type, and said CDH is obtained from *P. chrysosporium*.

2. The transgenic plant of claim 1, wherein said plant is selected from the group consisting of a monocotyledonous and dicotyledonous plant, grain crop, forage crop, root vegetable crop, woody plant, conifer, pine tree, poplar, willow, eucalyptus, acacia, oil palm, sugar cane, Jerusalem artichoke and perennial grass.

3. The transgenic plant of claim 2, wherein said root vegetable crop is selected from the group consisting of carrot, potato, sugar beets and yam.

4. The transgenic plant of claim 2, wherein said pine tree is selected from the group consisting of pine fir, loblolly pine, radiata pine and spruce.

5. The transgenic plant of claim 2, wherein said perennial grass is switch grass or miscanthus.

6. The transgenic plant of claim 1, wherein the cellulose in the cell wall of the transgenic plant is less crystalline than the cellulose in the cell wall of the wild type.

7. The transgenic plant of claim 1, wherein the lignin content in the cell wall of the transgenic plant is less than the lignin content in the cell wall of the wild type.

8. The transgenic plant of claim 1, wherein the transgenic plant is more amenable than the wild type for processing into a bio-fuel, wood, paper, textile or yarn product.

9. A method of making a bio-fuel, wood, paper, textile or yarn product, comprising: a) expressing a nucleic acid molecule encoding CDH in a plant, said CDH including a signal peptide sequence that can send said CDH to the plant cell wall; and b) processing the cellulose or hemicellulose portion of the plant into said product, wherein the cell wall of the transgenic plant is more water soluble than the cell wall of the wild type, and said CDH is obtained from *P. chrysosporium*.

10. The method of claim 9, wherein the product is a bio-fuel.

11. The method of claim 10, wherein said bio-fuel is ethanol or butanol.

12. The method of claim 11, wherein said bio-fuel is ethanol.

13. The transgenic plant of claim 1, wherein said plant is a woody plant.

14. The method of claim 9, wherein said plant is a woody plant.

15. A transgenic plant expressing a nucleic acid sequence encoding a cellobiose dehydrogenase (CDH) polypeptide, wherein said polypeptide is expressed in the cell wall of the plant using a nucleic acid sequence encoding a signal peptide, wherein the cell wall of the transgenic plant is more water soluble than the cell wall of the wild type and said CDH comprises SEQ ID NO: 6.

16. The transgenic plant of claim 15, wherein said plant is selected from the group consisting of a monocotyledonous and dicotyledonous plant, grain crop, forage crop, root vegetable crop, woody plant, conifer, pine tree, poplar, willow, *eucalyptus*, acacia, oil palm, sugar cane, Jerusalem artichoke and perennial grass.

17. The transgenic plant of claim 15, wherein the transgenic plant is more amenable than the wild type for processing into a bio-fuel, wood, paper, textile or yarn product.

18. A method of making a bio-fuel, wood, paper, textile or yarn product, comprising: a) expressing a nucleic acid molecule encoding CDH in a plant, said CDH including a signal peptide sequence that can send said CDH to the plant cell wall; and b) processing the cellulose or hemicellulose portion of the plant into said product, wherein the cell wall of the transgenic plant is more water soluble than the cell wall of the wild type and said CDH comprises SEQ ID NO: 6.

19. The method of claim 10, wherein said bio-fuel is ethanol or butanol.

* * * * *

UNITED STATES PATENT AND TRADEMARK OFFICE
CERTIFICATE OF CORRECTION

| | | |
|---|---|---|
| PATENT NO. | : 10,011,846 B2 | Page 1 of 1 |
| APPLICATION NO. | : 12/450443 | |
| DATED | : July 3, 2018 | |
| INVENTOR(S) | : Oded Shoseyov et al. | |

It is certified that error appears in the above-identified patent and that said Letters Patent is hereby corrected as shown below:

In the Claims

In Claim 19, Column 42 at Line 31, "The method of claim 10" should be changed to --The method of claim 18--.

Signed and Sealed this
Sixteenth Day of April, 2019

Andrei Iancu
*Director of the United States Patent and Trademark Office*

SEQUENCE LISTING

```
<160> NUMBER OF SEQ ID NOS: 8

<210> SEQ ID NO 1
<211> LENGTH: 1707
<212> TYPE: DNA
<213> ORGANISM: Chlorella virus

<400> SEQUENCE: 1
ttgacttata aaagagaaca catatttgtt tcgttaaaat aaattaacgc gaaaacgaaa      60
aacacaatgc tgcctctcaa aatcaagagt agcatactgt atgcggttat cttggccatt     120
aactttggga ttgctttcgc tcgtcattat atttcatgag tattggtatg catttgcgcc     180
tattcttgta ctcggcgctg cgtcttctct gtggtatatt gcgtgggtgc ttatgcatcg     240
tgtatactta ggtttcaaag gaaaacccgt gctgaccgcc cccaaagaac ctatgatgtt     300
cctcgtcaca gcgtatcgcg agacgaagga agaacttgat agaaccgtgg agtccgttac     360
gatgcaaaaa atagaccccg aggttagcaa gactgttgtt gttattgttg atggtgagaa     420
ggaaactgca cacgaactac gaaagtataa ccagtatgat gaaactttcg tcatcaaaga     480
tgcatatgag gattggcata ataagccaaa ggatgttaca attttcaaga aaatacataa     540
tggtattgac gtcgtatatc tcataaaaag tgagaacgcg ggaaaacgtg atagcgttgt     600
gcttgcacga actcttgcat acggaaatct gttcgaacat agtgaaaaca gacatgctat     660
gaaaatttca ggcgaattag acctcatatg gtctcgtttg gtaccgaaag ttacccgtat     720
gattggtatt gacgccgaca ctgttttcca cgaggattgc tctcaagctc ttcttgaaga     780
aatgaattat cccggtgata ggccggttga cggtgttgtt ggttatattg atattgagat     840
ggggaaaggt aaatctccct atcaaaaggc ttggatttgg ttccaaggaa ttggttatat     900
aatcggccag catgtgatgc gcgtatacca gagcaggata accgaaaagg taagttgttt     960
```

```
gtcgggcgct tgttacggta tttacgtccc taccatgtgc gaacctgagt tgttgaaaga   1020
atttaatacg cctcctcccc caaacgccgg tttgtttctt agtattcttg gttatgcttc   1080
cgaagatcgt agatcagtcg tcctgtcact atgtcgtgat aggaacgtcc gttttagaca   1140
ggcacttgat agtcgtgcgg tcgcttatac agtgcctcca gataacttta cagtttttat   1200
ctcacagagg cgtcgttggt ctcttggcac tgtatgcaat aatctatggc tctttcttta   1260
tggaaagaat ttgtatattt ccgaacgtat tatagctctt gttcaagtta ttggtttttct   1320 gttttcaccc ctttatctca tggttaacgt atatttgatt tatattctag tttctagatt   1380
cgatatcaaa ctgatttata tttctatccc aatgttcttg gtgtatctga ataacctttg   1440
catccctgtg tggtccccct tgcatgggttc tcttagaaat cgtctatcgt attatccaaa   1500
attgattatg gcattttttt attctccatg ggtttcagtc atcattcaag caaactccgt   1560
tatcaaaagt tttagtgttt cgtggggaaa aactgtggtt aaaacgactt ccgagacaac   1620
taaaattaca caaccaata cacttgtctg aaacgtatcg ttgtaaatat caatcacaca   1680
aaaaaaaaaa aaaaaaaaaa aaaaaaa                                      1707

<210> SEQ ID NO 2
<211> LENGTH: 809
<212> TYPE: DNA
<213> ORGANISM: Glomerella lindemuthiana

<400> SEQUENCE: 2
atgcacttct cgacccttttt tggcgccgcg gctactgctg ctctcgctgg cagcacgaac    60
gcaaggtacg tcgccggcgg ctccttgggc ccttgacaca gacacccag actgacacaa    120 ctcacagccc tctcgcccgt cgccaggttc ccgtgggcac acccatcctc cagtgcaccc   180
agcctggtct ggttgccctg acctacgacg acggtccctt caccttcacc ccgcagctcc   240
tcgacatctt gaagcagaac gacgtcaggg cgaccttttt cgtcaacggc aacaactggg   300
ccaacatcga ggccggatcc aaccccgaca ccatccgccg catgcgcgcc gacggccacc   360
tcgtcggctc tcacacgtac gctcacccgg acctcaacac gctctcctcc gcggaccgca   420
tctcccagat gcggcacgtc gaggaggcta cccgccgcat cgacggcttc gcgcccaagt   480
acatgcgcgc gccctacctg tcgtgcgacg cgggctgcca gggcgacctc ggcggcctcg   540
gataccacat catcgacacc aacctcgaca ccaaggacta cgagaacaac aagcccgaga   600
ccacgcacct ctcggccgag aagttcaaca acgagctgag cgccgacgtc ggcgccaaca   660
gctacattgt cctctcgcac gacgtccacg agcagacggt cgtctccctc acgcagaagc   720
tgattgacac gctcaagagc aagggctacc gcgccgtcac cgtcggcgag tgcctcggcg   780
acgccccgga gaactggtac aaggcgtaa                                     809

<210> SEQ ID NO 3
<211> LENGTH: 1707
<212> TYPE: DNA
<213> ORGANISM: Paramecium bursaria Chlorella virus 1

<400> SEQUENCE: 3
atgggtaaaa atataatcat aatggttttcg tggtacacca tcataacttc aaatctaatc    60
gcggttggag gagcctctct aatcttggct ccggcaatta ctgggtatgt tctacattgg   120
aatattgctc tctcgacaat ctggggagta tcagcttatg gtattttcgt ttttgggttt   180
ttccttgcac aagtttttatt ttcagaactg aacaggaaac gtcttcgcaa gtggatttct   240
ctcagaccta agggttggaa tgatgttcgt ttggctgtga tcattgctgg atatcgcgag   300
```

-continued

```
gatccttata tgttccagaa gtgcctcgag tctgtacgtg actctgatta tggcaacgtt    360
gcccgtctga tttgtgtgat tgacggtgat gaggacgatg atatgaggat ggctgccgtt    420
tacaaggcga tctacaatga taatatcaag aagcccgagt tgttctgtg tgagtcagac     480
gacaaggaag gtgaacgcat cgactctgat ttctctcgcg acatttgtgt cctccagcct    540
catcgtggaa aacgggagtg tctttatact gggtttcaac ttgcaaagat ggaccccagt    600
gtcaatgctg tcgttctgat tgacagcgat accgttctcg agaaggatgc tattctggaa    660
gttgtatacc cacttgcatg cgatcccgag atccaagccg ttgcaggtga gtgtaagatt    720
tggaacacag acactctttt gagtcttctc gtcgcttggc ggtactattc tgcgttttgt    780
gtggagagga gtgcccagtc ttttttcagg actgttcagt gcgttggggg gccactgggt    840
gcctacaaga ttgatatcat taaggagatt aaggacccct ggatttccca cgctttctt    900
ggtcagaagt gtacttacgg tgacgaccgc cggctaacca acgagatctt gatgcgtggt    960
aaaaaggttg tgttcactcc atttgctgtt ggttggtctg acagtccgac caatgtgttt   1020
cggtacatcg ttcagcagac ccgctggagt aagtcgtggt gccgcgaaat tggtacacc    1080
ctcttcgccg cgtggaagca cggttttgtct ggaatttggc tggcctttga atgtttgtat   1140
caaattacat acttcttcct cgtgatttac ctcttttctc gcctagccgt tgaggccgac   1200
cctcgcgccc agacagccac ggtgattgtg agcaccacgg ttgcattgat taagtgtggg   1260
tatttttcat tccgagccaa ggatattcgg gcgttttact ttgtgcttta tacatttgtt   1320
tacttttct gtatgattcc ggccaggatt actgcaatga tgacgctttg gacattggc     1380
tggggtactc gcggtggaaa cgagaagcct tccgttggca cccgggtcgc tctgtgggca   1440
aagcaatatc tcattgcata tatgtggtgg gccgcggttg ttggcgctgg agtttacagc   1500
atcgtccata actggatgtt cgattggaat tctctttctt atcgttttgc tttggttggt   1560
atttgttctt acattgtttt tattgttatt gtgctggtgg tttatttcac cggcaaaatt   1620
acgacttgga atttcacgaa gcttcagaag gagctaatcg aggatcgcgt tctgtacgat   1680
gcaactacca atgctcagtc tgtgtga                                        1707
```

<210> SEQ ID NO 4  
<211> LENGTH: 2085  
<212> TYPE: DNA  
<213> ORGANISM: Agrobacterium sp. ATCC 31749

<400> SEQUENCE: 4

```
attgggcgag ccctgcgggt tcactcctat acccgcaggg cagttcttca tttcaaaaa     60
tgatgttcag atgcgcgccc ggaacccgac gcgcagccga ccaactgcga ggttagggcg    120
atgtatttca gtgctgaagg tgacgttcag tcggtgctct atgtgaacct gacgattgcg    180
attggggcga tcctgtttgc ccttctcgct gatcccagaa agatggtcga caggttggcc    240
ttcagcatca tcatgttgct atcgcttggt gtctatatcg tatggcgggc aacggatacc    300
ttgccgccgc cggaactctc cctcgaaacg ctctggtgct acacctattt caccttcgag    360
ctgatctcgg tgctttatgc catggggtcc atcctcatac ttcttcgccg aaccgactgg    420
tcagccgttg ccgatcaggg agaggcatat cttgcaggca acccgcatgc gccgctcgtc    480
gatgtgttta tctgcactta caacgagccg ctgaacgttc tcgaaaaatc catcatcgcc    540
gcgcaggcga tggattatcc tcgactcgcg gtcttcgtct gtgacgacac acgtcgcggg    600
gaggtaagaa cctattgcga agcggcaggc gtgaactacg tcacacgtcc cgacaacaag    660
```

```
cacgccaagg caggaaatct caacaatgcg ctgctccaca ccaatgcgct ggaagaggtt      720
tccgacttca tcatggtcct cgacgcggat tttgcccccc aggcaaactt cctgcggcgc      780
gtgacgggtc tcttttcgga cccgaaggtg gctgtcgtcc agacgcctca attctatttc      840
aacagtgatc caattcagca caatctcggt atagacaaga gcttcgtgga cgaccagcgg      900
gtcttcttcg acgatttcca gccggccaag gatgccgttg gttgcgcttt tcgcgtcggc      960
accagcttcg tcgtacgccg cgccgcggta atggtattg gtggtttccc tacggatgcg     1020
cttaccgaag acatgctgct gacatatcgc ctgatggaaa ggggatatgt cacgcgctgg     1080
ctgaatgaga agtggagcgt tggattgtcg gcggaaggtg tacccgaata catcacccag     1140
cgcacccgct ggtgtctcgg cacgatccag atcgggcttc tgcggaccgg acctctctgg     1200
cgtggaaatt ttacgctgac gcagcggctg cactatctgc atggactttt ctgctggctg     1260
tcgaagccgc ttatcctgtg cctgctgctt gcgccgtcca tctattggct gacgggcgtg     1320
tcggcgctgc aggtcgatga gctgatgttc atgaagctcg gcctgtcatc tcttgcgctt     1380
ttctggacct attccacctg gatatccggc aagaggacgc ttcctctctt caccgaagtc     1440
acccacgccc tgaccgctgt acccattacc atcacgcttt tcaggcaat ccgtaaaccg     1500 ttcgggcgcc cgttcaaagt caccgaaaag ggaggagacc gatcccaggt ccgtgtccac     1560
ctcccgacgg ggatttttt cgctttcgtg accctgtctt cggccgtctc catcgtgctg     1620
gctgtctatg gtctggatgc tccgtccgag ctgtcctcgc gggactgcct caatctgatc     1680
tggtccgccg tcgcgatggt tatcgcattc accagcttca tttgctgcat gaattgccg      1740 cgtttcggca aggaggaaat gatcggagtg gattttcgcg ggcagttgcg gtccgcatcc     1800
tcaacgagac cggtgcgtat caccggcctc tcgacggaaa acatcacact ggctgcggtt     1860
ccgtcttcca gcgatgtaaa ggatgttttc gtaccggagg cggggtggat gcggatcagc     1920
cctgcggagc acgcgcagaa ctccggaaag ttcgatattc atccaagcga cgagcagcgc     1980
cggtccattt tgcgcctgtt gtttcgcaag gctcctgaaa atgtcgcgga acagggcgac     2040
ctgatgaaat ccatgcggat tcttctcgca cgggcattcg ggtga                    2085
```

<210> SEQ ID NO 5
<211> LENGTH: 1406
<212> TYPE: DNA
<213> ORGANISM: Erwinia amylovora

<400> SEQUENCE: 5

```
ctgcagcgat catggttatt tataagggat tgttatgtcc tgaaaaccac acaacagaac       60
cagagtgatt tcaaaaaata aaaagctatt aatatacaga ccttcagcaa gaaggtattc      120 gaaataaccct gtgaggatat ttatgtcaga ttataattat aaaccaacgc tgtggactcg      180
tgccgatgca ttgaaagttc atgaggatga cccaaccaca actcaaccgg ttattgacat      240
tgcattcccg gtaatgagtg aagaagtctt tatttgggat accatgccat tgcgagactt      300
cgacggagag attatctctg taaatggttg gtgtattatt tttacgctaa cagcagatcg      360
caacactgat aatccgcaat tccaggatga aaatggcaat tatgatatta ctcgtgactg      420
ggaagacaga catggtcgtg cgcgtatttg ttattggtac tcacgcaccg gtaaagactg      480 gattttggc ggtcgggtaa tggccgaagg tgtcgcaccg acgacgcgtg agtgggccgg      540
aaccccgatc ctttttaaacg atcggggcga tattgacctg tattataccgt gtcactcc      600 gggtgcaacc attgccaaag tgcgcggtaa aatcgtcact tccgatcaaa gtgtaagcct      660
ggaaggtttt cagcaggtta catcacttt ctctgctgac gggactattt accagacgga      720
```

```
agagcagaac gctttctgga acttccgtga cccaagccca ttcattgaca ggaatgatgg      780
caaattatat atgctgtttg aaggaaacgt ggcggggccg cgcggttcgc acgaaattac      840
ccaggctgag atgggtaatg tgccgccggg ttatgaagat gtgggtggcg caaaatatca      900
ggcaggctgt gttggtctgg ctgtggccaa agacctgtca ggcagtgagt ggcaaatcct      960
gcctccgctg atcaccgctg ttggcgtaaa cgatcagact gaacgccctc attttgtctt     1020
ccaggatggt aaatactatc tgttcaccat tagccataag tacacttttg ccgataacct     1080
gaccggccct gatggagtgt atggctttgt aagcgataaa cttaccggcc cttacacgcc     1140
gatgaatagc tccgggctgg tgctgggcaa cccgtcttca aacctttcc agacatattc      1200 acactatgtt atgcctaatg ggctggtcac ttcctttatt gacagtgttc cgtggaaagg     1260
taaggactat cgcattggcg gtactgaagc tccgaccgta aaaattctgt tgaaaggcga     1320
tcgctcattt attgttgata gcttcgatta tggatatatt ccggcaatga aagacattac     1380
tttaaaataa gtctgttgtc gatatc                                          1406
```

<210> SEQ ID NO 6
<211> LENGTH: 2319
<212> TYPE: DNA
<213> ORGANISM: Phanerochaete chrysosporium

<400> SEQUENCE: 6

```
atgctaggtc gatcgttact tgcgcttctg ccttttgtag gcctcgcgtt ctcgcagagt       60
gcctcacagt ttaccgaccc taccacagga ttccagttca ctggtatcac cgaccctgtt      120
catgacgtga cctacggctt cgttttcccc cctctggcca cctccggagc gcaatccact      180
gagttcatcg agaggttgt tgcccccatc gcatcaaaat ggattggtat tgccctcggt       240
ggcgccatga caacgaccct gctacttgtg gcttgggcca acggcaacca aattgtttcc      300
tccactcgct gggctactgg ctatgtacag ccgactgcat atacgggaac tgccactttg      360
acaacactcc ctgagacaac catcaactcc acgcactgga gtgggtctt caggtgtcag       420 ggctgcactg agtggaacaa tggcggcgga atcgacgtca ctagccaggg cgttctggcg      480
tgggcattct ccaacgtcgc cgtcgacgac ccctccgacc cgcagagtac cttcagcgag      540
cacaccgact tcggcttctt cggaattgac tactcgaccg acagcgccaa ctaccagaac      600
taccttaatg gcgactccgg caaccctacg accacgagca ccaagcccac aagcacgagc      660
agctcagtca cgactggacc cactgttttct gctacacctt acgattacat catcgtcggt      720
gctggtcctg gcggtatcat tgcagctgat cgtctgtcgg aggctggcaa gaaggttctc      780
cttctcgagc gcggtggccc tagcaccaag cagaccggtg aacgtatgt cgctccatgg      840 gctactagca gtggtctaac gaagttcgat attcccggac tgttcgagtc cttgttcact      900
gattccaacc ccttctggtg gtgcaaagac atcacagtct cgctggttg cctggtcggc       960 ggcggtactt cggtcaacgg agctctctac tggtacccta cgacggcga cttctcctcg      1020 agcgttggtt ggccaagcag ctggaccaac cacgccccgt acacgagcaa gctttcgtct     1080
cgtctcccca gtacggacca cccttcgact gatggccagc gctaccttga gcaatcattc     1140
aacgtcgtgt ctcaacttct caaaggccaa ggctacaacc aggccaccat caacgacaac     1200
cccaactaca aggaccacgt cttcggctac agcgcattcg atttccttaa cggcaagcgt     1260
gctggtccag tcgccaccta cctccagacg gcattggctc gccccaactt cactttcaag     1320
accaatgtca tggtctcgaa cgttgtccgc aacggctcgc agatcctcgg tgtccagacg     1380
```

-continued

| | |
|---|---|
| aacgacccga cgctcggccc caacggtttc atccccgtga ccccgaaggg gcgtgtcatc | 1440 |
| ctctctgctg gtgcatttgg cacttcgcgc attctcttcc aaagcggtat tggccccacg | 1500 |
| gatatgattc agactgttca gagcaacccg accgccgccg ccgcgctccc gccgcagaac | 1560 |
| cagtggatca acctcccagt cggcatgaac gcacaggaca cccctcgat caacctggtc | 1620 |
| ttcacccacc ccagcatcga tgcctatgag aactgggctg acgtctggag caacccgcgc | 1680 |
| ccggctgacg ctgcacagta cctcgcgaac cagtccggtg tcttcgcagg tgcttctccc | 1740 |
| aaactcaact tctggcgcgc atactctggt tcggatggct ttacccgtta tgcccagggg | 1800 |
| acggtgcgcc cgggcgcagc ctccgtgaac tcctcgctgc cgtacaacgc gagccagatc | 1860 |
| ttcacgatca ccgtgtacct ctctacgggc atccagtcgc gtgggcgcat cggcatcgat | 1920 |
| gcagcgctcc gcggtacggt gctcacaccg ccgtggctcg tgaatccggt cgacaagacc | 1980 |
| gtgctcctgc aggcgctgca cgacgtcgtc tcgaacatag ggtcgattcc cggcctgacg | 2040 |
| atgatcacgc ccgacgtcac gcagacactc gaggagtacg tcgatgcgta cgaccccgcg | 2100 |
| acgatgaact cgaaccactg ggtctcgtcc acgacgatcg gctcatctcc ccagagcgcg | 2160 |
| gtagtcgatt cgaacgtcaa ggtctttggc acgaacaacc tgtttatcgt cgacgcaggt | 2220 |
| atcattcccc acctgcccac gggcaacccc cagggcacgc tcatgtctgc cgccgagcag | 2280 |
| gcggccgcga agatcctcgc gcttgcggga ggtccttga | 2319 |

<210> SEQ ID NO 7
<211> LENGTH: 1791
<212> TYPE: DNA
<213> ORGANISM: Chlorella virus

<400> SEQUENCE: 7

| | |
|---|---|
| atgtgtggca tctttggagc agtgtcaaac aataactcta tcgaggtgtc aataaagggt | 60 |
| attcaaaagc tagaatatcg cgggtatgat tcgtgcggta ttgcgtatgc agatggagac | 120 |
| ggtgtaatcg agcgtatacg ttcaattgat ggaattgaag atcttcgcaa gaaaacactt | 180 |
| gaagaatcct caccggttgc cattgctcac tctaggtgga gcaccaccgg aattccatcg | 240 |
| gtggtgaacg cacatcctca tatttctcgc ggaaccagtg ggtgtgagtc tcgtatcgcg | 300 |
| gtagtccaca atggtatcat tgaaaactat cagcagatcc gaaaatatct catcaatctc | 360 |
| ggttatacgt tgatagtca acggacaca gaggtcattg cacatttgat cgattctcag | 420 |
| tacaatggga atatcttgca caccgtccaa atggctgtca agcacctgaa gggctcttat | 480 |
| gcaattgcag ttatgtgtca taagagtct ggtaaaatag tcgtggcgaa acagaagtca | 540 |
| cccctcgtac ttggaatcgg ctcagatggt gcttactaca ttgcttcgga cgtgctggcg | 600 |
| ctgccgacaa ataaagttgt ttatatttca gatggtttct ccgcagaact atctccaggg | 660 |
| agtatgacca tttacgatcc tgatggaaat gaagtggaat atgaagtaga ggacgttgaa | 720 |
| atggaacaaa ctagtatgtc tctcgataac tttgatcatt acatgattaa ggaaattaat | 780 |
| gagcaaccaa tcagtattct aaacactata aaaaataaag ggttctatgc agaaatattc | 840 |
| ggtgatttgg cgcatgaaat cttccaaaaa atagacaaca tcctgatact ggcttgtggt | 900 |
| acaagttatc acgccggtct tgtaggaaaa cagtggatag agaccatcgc gagaatcccc | 960 |

```
gtggatgttc acatcgcgag cgaatacgaa cctacaattc cgagagcgaa cacattggta    1020
atcactattt cacagtcggg tgaaactgcg gacacgatag cggctttgca acgggcccag    1080
aacgcaggga tgatttatac gttgtgcatt tgcaactcgc caaagagcac tcttgtccgc    1140
gagagcgtta tgaagtacat aacgaaatgt gggtctgagg tgtcagtagc atcaacgaag    1200
gcgtttacct cacagctcgt agtactgtac atgctggcaa acgtattggc aaataaaacc    1260
gatgatttgc tgggagacct cccacaggca atagaacggg tgatttgttt gacaaatgac    1320
gaaatgaaac gatgggctga cgaaatttgc actgcgaaat ctgcgatctt cctgggaaga    1380
ggactaaacg caccagttgc ctttgaggga gcgctgaagc tcaaagaaat ctcttacatt    1440
catgcagagg gcttcctggg aggtgagttg aaacatggtc ccctcgcact ccttgatgac    1500
aagattcctg ttatcgtaac cgtagcagat catgcttatt tggaccatat caaagcaaat    1560
attgacgaag tgcttgcgag gaacgttacg gtatacgcca tagtagacca gtatgtgaac    1620
attgagcccc aggaacgcct tcacgtcgtc aaggttccgt ttgtatccaa agaattttct    1680
ccgataattc acactatccc gatgcaactg ctttcgtatt acgtggcaat taagcttggg    1740
aagaacgttg acaaaccaag gaatcttgca aaatccgtga ctacctttta a             1791
```

<210> SEQ ID NO 8
<211> LENGTH: 596
<212> TYPE: PRT
<213> ORGANISM: Chlorella virus

<400> SEQUENCE: 8

```
Met Cys Gly Ile Phe Gly Ala Val Ser Asn Asn Ser Ile Glu Val
1               5                   10                  15

Ser Ile Lys Gly Ile Gln Lys Leu Glu Tyr Arg Gly Tyr Asp Ser Cys
            20                  25                  30

Gly Ile Ala Tyr Ala Asp Gly Asp Gly Val Ile Glu Arg Ile Arg Ser
        35                  40                  45

Ile Asp Gly Ile Glu Asp Leu Arg Lys Lys Thr Leu Glu Glu Ser Ser
    50                  55                  60

Pro Val Ala Ile Ala His Ser Arg Trp Ser Thr Thr Gly Ile Pro Ser
65                  70                  75                  80

Val Val Asn Ala His Pro His Ile Ser Arg Gly Thr Ser Gly Cys Glu
                85                  90                  95

Ser Arg Ile Ala Val Val His Asn Gly Ile Ile Glu Asn Tyr Gln Gln
            100                 105                 110

Ile Arg Lys Tyr Leu Ile Asn Leu Gly Tyr Thr Phe Asp Ser Gln Thr
        115                 120                 125

Asp Thr Glu Val Ile Ala His Leu Ile Asp Ser Gln Tyr Asn Gly Asn
    130                 135                 140

Ile Leu His Thr Val Gln Met Ala Val Lys His Leu Lys Gly Ser Tyr
145                 150                 155                 160

Ala Ile Ala Val Met Cys His Lys Glu Ser Gly Lys Ile Val Val Ala
                165                 170                 175

Lys Gln Lys Ser Pro Leu Val Leu Gly Ile Gly Ser Asp Gly Ala Tyr
            180                 185                 190

Tyr Ile Ala Ser Asp Val Leu Ala Leu Pro Thr Asn Lys Val Val Tyr
        195                 200                 205

Ile Ser Asp Gly Phe Ser Ala Glu Leu Ser Pro Gly Ser Met Thr Ile
    210                 215                 220
```

-continued

```
Tyr Asp Pro Asp Gly Asn Glu Val Glu Tyr Glu Val Asp Val Glu
225                 230                 235                 240

Met Glu Gln Thr Ser Met Ser Leu Asp Asn Phe Asp His Tyr Met Ile
                245                 250                 255

Lys Glu Ile Asn Glu Gln Pro Ile Ser Ile Leu Asn Thr Ile Lys Asn
            260                 265                 270

Lys Gly Phe Tyr Ala Glu Ile Phe Gly Asp Leu Ala His Glu Ile Phe
        275                 280                 285

Gln Lys Ile Asp Asn Ile Leu Ile Leu Ala Cys Gly Thr Ser Tyr His
    290                 295                 300

Ala Gly Leu Val Gly Lys Gln Trp Ile Glu Thr Ile Ala Arg Ile Pro
305                 310                 315                 320

Val Asp Val His Ile Ala Ser Glu Tyr Glu Pro Thr Ile Pro Arg Ala
                325                 330                 335

Asn Thr Leu Val Ile Thr Ile Ser Gln Ser Gly Glu Thr Ala Asp Thr
            340                 345                 350

Ile Ala Ala Leu Gln Arg Ala Gln Asn Ala Gly Met Ile Tyr Thr Leu
        355                 360                 365

Cys Ile Cys Asn Ser Pro Lys Ser Thr Leu Val Arg Glu Ser Val Met
    370                 375                 380

Lys Tyr Ile Thr Lys Cys Gly Ser Glu Val Ser Val Ala Ser Thr Lys
385                 390                 395                 400

Ala Phe Thr Ser Gln Leu Val Val Leu Tyr Met Leu Ala Asn Val Leu
                405                 410                 415

Ala Asn Lys Thr Asp Asp Leu Leu Gly Asp Leu Pro Gln Ala Ile Glu
            420                 425                 430

Arg Val Ile Cys Leu Thr Asn Asp Glu Met Lys Arg Trp Ala Asp Glu
        435                 440                 445

Ile Cys Thr Ala Lys Ser Ala Ile Phe Leu Gly Arg Gly Leu Asn Ala
    450                 455                 460

Pro Val Ala Phe Glu Gly Ala Leu Lys Leu Lys Glu Ile Ser Tyr Ile
465                 470                 475                 480

His Ala Glu Gly Phe Leu Gly Gly Glu Leu Lys His Gly Pro Leu Ala
                485                 490                 495

Leu Leu Asp Asp Lys Ile Pro Val Ile Val Thr Val Ala Asp His Ala
            500                 505                 510

Tyr Leu Asp His Ile Lys Ala Asn Ile Asp Glu Val Leu Ala Arg Asn
        515                 520                 525

Val Thr Val Tyr Ala Ile Val Asp Gln Tyr Val Asn Ile Glu Pro Gln
    530                 535                 540

Glu Arg Leu His Val Val Lys Val Pro Phe Val Ser Lys Glu Phe Ser
545                 550                 555                 560

Pro Ile Ile His Thr Ile Pro Met Gln Leu Leu Ser Tyr Tyr Val Ala
                565                 570                 575

Ile Lys Leu Gly Lys Asn Val Asp Lys Pro Arg Asn Leu Ala Lys Ser
            580                 585                 590

Val Thr Thr Phe
        595
```